United States Patent
Lowe, III

(10) Patent No.: US 6,506,780 B2
(45) Date of Patent: Jan. 14, 2003

(54) BENZOPHENONES AND SULFONES AS INHIBITORS OF GLYCINE UPTAKE

(75) Inventor: John A. Lowe, III, Stonington, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 09/897,261

(22) Filed: Jul. 2, 2001

(65) Prior Publication Data
US 2002/0052401 A1 May 2, 2002

Related U.S. Application Data
(60) Provisional application No. 60/215,692, filed on Jun. 30, 2000.

(51) Int. Cl.[7] .................. C07D 213/46; A61P 25/18
(52) U.S. Cl. .................. 514/354; 514/372; 514/448; 514/465; 546/328; 548/200; 549/57; 549/62; 549/65; 549/468; 549/471
(58) Field of Search .................. 549/62, 65, 57, 549/468, 471; 514/448, 465, 354, 372; 546/328; 548/200; 562/433

(56) References Cited

U.S. PATENT DOCUMENTS
6,191,165 B1 * 2/2001 Ognyanov et al. .......... 514/423

FOREIGN PATENT DOCUMENTS
WO          9745115 WO    4/1997

OTHER PUBLICATIONS

Richard Bergeron, et al., Modulation of N-methyl-D-aspartate receptor function by glycine transport, vol. 95, pp. 15730-1534, Dec. 1998.

Angus Brown, et al., Discover and SAR of Org 24598-A Selective Glycine Uptake Inhibitor, Bioorganic & Medicinal Chemistry Letters 11 (2201) 2007-2009.

H. J. Herdon, et al., Pharmacological assessment of the role of the glycine transporter GlyT-1 in mediating high-affinity glycine uptake by rat cerebral cortex and cerebellum synptosomes, Neuropharmacology 41 (2001) 88-96.

* cited by examiner

*Primary Examiner*—Joseph K. McKane
*Assistant Examiner*—Kamal Saeed
(74) *Attorney, Agent, or Firm*—P. C. Richardson; P. H. Ginsburg; A. D. Joran

(57) ABSTRACT

This invention relates to a series of substituted benzophenone and sulfone compounds of the formula I

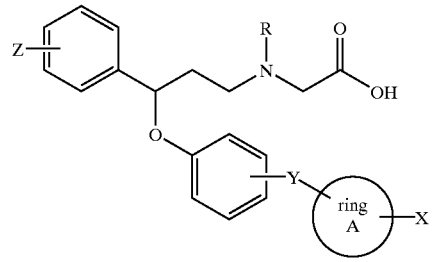

wherein ring A, Z, Y, R and X are defined as in the specification, that exhibit activity as glycine transport inhibitors, their pharmaceutically acceptable salts, pharmaceutical compositions containing them, and their use for the enhancement of cognition and the treatment of the positive and negative symptoms of schizophrenia and other psychoses in mammals, including humans.

17 Claims, No Drawings

BENZOPHENONES AND SULFONES AS INHIBITORS OF GLYCINE UPTAKE

This application claims the benefit of United States provisional patent application No. 60/215,692, filed Jun. 30, 2000.

BACKGROUND

The present invention relates to certain benzophenones and sulfones containing a pendant amino acid side chain that exhibit activity as inhibitors of the glycine type-1 transporter, to pharmaceutical compositions containing them and to their use in the treatment of central nervous system disorders, cognitive disorders, schizophrenia, depression, anxiety, dementia and other disorders in mammals, including humans.

Schizophrenia, a progressive neurological disease, is manifested in its early stages as thought disorders such as hallucinations, paranoid delusions, and bizarre thought patterns, collectively known as positive symptoms. These easily recognizable symptoms gave the disease the historical name "madness". As the disease progresses, negative symptoms, such as social withdrawal and anhedonia, and cognitive symptoms such as dementia become more apparent. Only about one-third of schizophrenic patients can be treated successfully and returned to society, while the remainder are generally institutionalized. The burden on society of this devastating illness and the toll it takes on family members of affected patients make it one of the most costly of all CNS diseases.

Pharmacological treatment for schizophrenia has traditionally involved blockade of the dopamine system, which is thought to be responsible for its positive symptoms. Such treatment, however, ignores the negative and cognitive aspects of the disease. Another neurotransmitter system believed to play a role in schizophrenia is the glutamate system, the major excitatory transmitter system in the brain. This hypothesis is based on the observation that blockade of the glutamate system by compounds such as PCP ("angel dust") can replicate many of the symptoms of schizophrenia, including its positive, negative, and cognitive aspects. If schizophrenia involves a deficit of glutamatergic transmission, augmentation of the glutamate system, and specifically the NMDA receptor, may be beneficial. While glutamate is the principle agonist at NMDA receptors, glycine is required as a co-agonist to set the "tone" of the receptor for its response to glutamate. Enhancing this "tone" by increasing the effect of glycine would augment NMDA neurotransmission, and provide potential benefit in the treatment of schizophrenia.

A specific mechanism for augmenting the glycinergic "tone" of the NMDA receptor was disclosed recently by Bergeron, et al. (*Proc. Natl. Acad. Sci. USA*, 95, 15730, (1998)). This group showed that a specific and potent inhibitor of the glycine type-1 transporter (GlyT1) responsible for removing glycine from the synapse at the NMDA receptor, termed NFPS (WO 97/45115), can enhance NMDA receptor function. For example, NFPS increased the post synaptic current driven by the NMDA receptor, an effect blocked by both a specific NMDA-site antagonist and a glycine-site antagonist. Even though glycine levels in the brain are high relative to the amount required to act as an NMDA receptor co-agonist, this work shows that GlyT1 removes glycine efficiently at the synapse, and that inhibition of GlyT1 can augment NMDA receptor function. The authors establish the feasibility of using a GlyT1 inhibitor as a treatment for schizophrenia through its augmentation of glutamatergic neurotransmission.

SUMMARY OF THE INVENTION

The present invention relates to compounds of the formula I

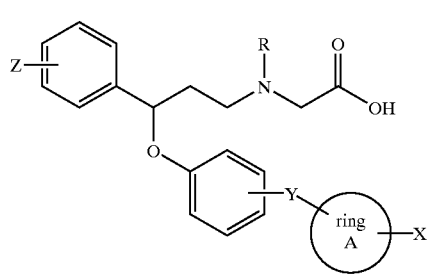

wherein ring A is phenyl, naphthyl, benzothienyl, benzofuranyl, or thienyl, or ring A is a monocyclic aryl or heteroaryl ring containing from zero to four heteroatoms and not containing any adjacent ring oxygen atoms; or ring A is a bicyclic aryl or heteroaryl ring containing from zero to five heteroatoms and not containing any adjacent ring oxygen atoms; and Y is C=O or $SO_2$ and is attached to the phenoxy group depicted in formula I at the meta or para position;

X and Z are independently selected from hydrogen, $(C_1-C_6)$ alkyl optionally substituted with from one to seven fluorine atoms, and $(C_1-C_6)$alkoxy optionally substituted with from one to seven fluorine atoms, wherein the number of fluorine substituents on the foregoing $(C_1-C_6)$ alkyl and $(C_1-C_6)$ alkoxy groups can not exceed the number of positions in such groups that are available for substitution;

or X and Z are independently selected from carboxy, carbo-$(C_1-C_6)$alkoxy, carboxamido, $(C_1-C_6)$alkylthio, sulfoxyl, sulfonyl, halo, nitro, cyano, amino, $(C_1-C_6)$ alkylamino and di[$(C_1-C_6)$ alkyl]amino; and R is hydrogen or ($C_1$ to $C_6$) alkyl, preferably hydrogen or methyl;

and the pharmaceutically acceptable salts of such compounds.

In a more specific embodiment of this invention, Y is C=O.

In another more specific embodiment of this invention, Y is $SO_2$.

In a preferred embodiment of this invention, ring A is selected from phenyl, naphthyl and benzothienyl.

In another preferred embodiment of this invention, X is para-trifluoromethyl, para-methyl or para-chloro.

Other specific compounds of the present invention include:

{[3-(3-Benzoyl-phenoxy)-3-phenyl-propyl]-methylamino}-acetic acid;

(Methyl-{3-[3-(naphthalene-2-carbonyl)-phenoxy]-3-phenyl-propyl}-amino)-acetic acid;

(Methyl-{3-[3-(4-methyl-benzoyl)-phenoxy]-3-phenyl-propyl}-amino)-acetic acid;

({3-[3-(4-Methoxy-benzoyl)-phenoxy]-3-phenyl-propyl}-methyl-amino)-acetic acid;

({3-[3-(4-Chloro-benzoyl)-phenoxy]-3-phenyl-propyl}-methyl-amino)-acetic acid;

(Methyl-{3-phenyl-3-[3-(thiophene-3-carbonyl)-phenoxy]-propyl}-amino)-acetic acid;

({3-[3-(2-Methoxy-benzoyl)-phenoxy]-3-phenyl-propyl}-methyl-amino)-acetic acid;
({3-[3-(Dichloro-benzoyl)-phenoxy]-3-phenyl-propyl}-methyl-amino)-acetic acid;
(Methyl-{3-phenyl-3-[3-(3-trifluoromethyl-benzoyl)-phenoxy]-propyl}-amino)-acetic acid;
Methyl-{3-[3-(3-methyl-benzoyl)-phenoxy]-3-phenyl-propyl}-amino)-acetic acid;
({3-[3-(2,3-Dimethyl-benzoyl)-phenoxy]-3-phenyl-propyl})-methyl-amino)-acetic acid;
({3-[3-(3-Methoxy-benzoyl)-phenoxy]-3-phenyl-propyl}-methyl-amino)-acetic acid;
(Methyl-{3-phenyl-3-[3-(4-trifluoromethyl-benzoyl)-phenoxy]-propyl}-amino)-acetic acid;
({3-[3-(2,4-Difluoro-benzoyl)-phenoxy]-3-phenyl-propyl}-methyl-amino)-acetic acid;
(Methyl-{3-[3-(naphthalene-1-carbonyl)-phenoxy]-3-phenyl-propyl}-amino)-acetic acid;
({3-[3-(Benzo[b]thiophene-2-carbonyl)-phenoxy]-3-phenyl-propyl}-methyl-amino)-acetic acid;
({3-[3-(Benzofuran-2-carbonyl)-phenoxy]-3-phenyl-propyl}-methyl-amino)-acetic acid;
({3-[3-(4-Fluoro-benzoyl)-phenoxy]-3-phenyl-propyl}-methyl-amino)-acetic acid;
({3-[3-(2-Fluoro-benzoyl)-phenoxy]-3-phenyl-propyl}-methyl-amino)-acetic acid;
({3-(4-Fluoro-phenyl)-3-[3-(4-methyl-benzoyl)-phenoxy]-propyl}-methyl-amino)-acetic acid;
{[3-[3-(4-Chloro-benzoyl)-phenoxy]-3-(4-fluoro-phenyl)-propyl]-methyl-amino}-acetic acid;
({3-(4-Fluoro-phenyl)-3-[3-(4-trifluoromethyl-benzoyl)-phenoxy]-propyl}-methyl-amino)-acetic acid;
({3-(4-Fluoro-phenyl)-3-[3-(4-methoxy-benzoyl)-phenoxy]-propyl}-methyl-amino)-acetic acid;
({3-(4-Fluoro-phenyl)-3-[3-(naphthalene-2-carbonyl)-phenoxy]-propyl}-methyl-amino)-acetic acid;
({3-(4-Fluoro-phenyl)-3-[3-(naphthalene-1-carbonyl)-phenoxy]-propyl}-methyl-amino)-acetic acid;
{[3-[3-(2,3-Dimethyl-benzoyl)-phenoxy]-3-(4-fluoro-phenyl)-propyl]-methyl-amino}-acetic acid;
{[3-[3-(2-Fluoro-benzoyl)-phenoxy]-3-(4-fluoro-phenyl)-propyl]-methyl-amino}-acetic acid;
([3-[3-(2,4-Difluoro-benzoyl)-phenoxy]-3-(4-fluoro-phenyl)-propyl]-methyl-amino)-acetic acid;
({3-(4-Fluoro-phenyl)-3-[3-(3-methyl-benzoyl)-phenoxy]-propyl}-methyl-amino)-acetic acid;
({3-(4-Fluoro-phenyl)-3-[3-(thiophene-3-carbonyl)-phenoxy]-propyl}-methyl-amino)-acetic acid;
{[3-[3-(Benzo[b]thiophene-2-carbonyl)-phenoxy]-3-(4-fluoro-phenyl)-propyl]-methyl-amino}-acetic acid;
({3-(4-Fluoro-phenyl)-3-[3-(pyridine-2-carbonyl)-phenoxy]-propyl}-methyl-amino)-acetic acid;
({3-(4-Fluoro-phenyl)-3-[3-(thiazole-2-carbonyl)-phenoxy]-propyl}-methyl-amino)-acetic acid;
{3-(4-Fluoro-phenyl)-3-[3-(5-methyl-thiazole-2-carbonyl)-phenoxy]-propyl}-methyl-amino)-acetic acid;
{[3-[3-(Benzothiazole-2-carbonyl)-phenoxy]-3-(4-fluoro-phenyl)-propyl]-methyl-amino}-acetic acid;
({3-(4-Fluoro-phenyl)-3-[3-(5-methyl-pyridine-2-carbonyl)-phenoxy]-propyl}-methyl-amino)-acetic acid;
({3-(4-Chloro-phenyl)-3-[3-(4-methyl-benzoyl)-phenoxy]-propyl}-methyl-amino)-acetic acid;
({3-(4-Chloro-phenyl)-3-[3-(4-methoxy-benzoyl)-phenoxy]-propyl}-methyl-amino)-acetic acid;
{[3-[3-(4-Chloro-benzoyl)-phenoxy]-3-(4-chloro-phenyl)-propyl]-methyl-amino}-acetic acid;
({3-(4-Chloro-phenyl)-3-[3-(4-trifluoromethyl-benzoyl)-phenoxy]-propyl}-methyl-amino)-acetic acid;
({3-(4-Fluoro-phenyl)-3-[3-(3-methyl-pyridine-2-carbonyl)-phenoxy]-propyl}-methyl-amino)-acetic acid;
({3-(4-Chloro-phenyl)-3-[3-(2-fluoro-benzoyl)-phenoxy]-propyl}-methyl-amino)-acetic acid;
({3-(4-Chloro-phenyl)-3-[3-(2,4-difluoro-benzoyl)-phenoxy]-propyl}-methyl-amino)-acetic acid;
({3-(4-Chloro-phenyl)-3-[3-(2,3-dimethyl-benzoyl)-phenoxy]-propyl}-methyl-amino)-acetic acid;
({3-(4-Chloro-phenyl)-3-[3-(thiophene-3-carbonyl)-phenoxy]-propyl}-methyl-amino)-acetic acid;
{[3-[3-(Benzo[b]thiophene-2-carbonyl)-phenoxy]-3-(4-chloro-phenyl)-propyl]-methyl-amino}-acetic acid;
({3-(4-Fluoro-phenyl)-3-[3-(pyridine-4-carbonyl)-phenoxy]-propyl}-methyl-amino)-acetic acid;
{[3-[3-(3,5-Bis-trifluoromethyl-benzoyl)-phenoxy]-3-(4-fluoro-phenyl)-propyl]-methyl-amino}-acetic acid;
({3-(4-Chloro-phenyl)-3-[3-(thiazole-2-carbonyl)-phenoxy]-propyl}-methyl-amino)-acetic acid;
({3-(4-Chloro-phenyl)-3-[3-(5-methyl-thiazole-2-carbonyl)-phenoxy]-propyl}-methyl-amino)-acetic acid;
{3-(4-Fluoro-phenyl)-3-[3-(4-isopropyl-benzoyl)-phenoxy]-propyl}-methyl-amino)-acetic acid;
({3-(4-Chloro-phenyl)-3-[3-(pyridine-4-carbonyl)-phenoxy]-propyl}-methyl-amino)-acetic acid;
{[3-[3-(2,6-Difluoro-benzoyl)-phenoxy]-3-(4-fluoro-phenyl)-propyl]-methyl-amino}-acetic acid;
{[[3-(4-Benzoyl-phenoxy)-3-(4-fluoro-phenyl)-propyl]-methyl-amino}-acetic aci;
({3-(4-Fluoro-phenyl)-3-[3-(pyridine-3-carbonyl)-phenoxy]-propyl}-methyl-amino)-acetic acid;
({3-(4-Chloro-phenyl)-3-[3-(pyridine-3-carbonyl)-phenoxy]-propyl}-methyl-amino)-acetic acid;
{[3-[3-(3,4-Difluoro-benzoyl)-phenoxy]-3-(4-fluoro-phenyl)-propyl]-methyl-amino}-acetic acid;
{[3-[3-(3,5-Difluoro-benzoyl)-phenoxy]-3-(4-fluoro-phenyl)-propyl]-methyl-amino}-acetic acid;
({3-(4-Chloro-phenyl)-3-[3-(3,5-difluoro-benzoyl)-phenoxy]-propyl}-methyl-amino)-acetic acid;
{3-(4-Chloro-phenyl)-3-[3-(3,4-difluoro-benzoyl)-phenoxy]-propyl}-methyl-amino)-acetic acid;
{[3-(4-Benzoyl-phenoxy)-3-p-tolyl-propyl]-methyl-amino}-acetic acid;
(Methyl-{3-[3-(4-methyl-benzoyl)-phenoxy]-3-p-tolyl-propyl}-amino)-acetic acid;
({3-[3-(4-Methoxy-benzoyl)-phenoxy]-3-p-tolyl-propyl}-methyl-amino)-acetic acid;
({3-[3-(4-Chloro-benzoyl)-phenoxy]-3-p-tolyl-propyl}-methyl-amino)-acetic acid;
(Methyl-{3-[3-(5-methyl-thiazole-2-carbonyl)-phenoxy]-3-p-tolyl-propyl}-amino)-acetic acid;
{[3-(3-Benzoyl-phenoxy)-3-(3-trifluoromethyl-phenyl)-propyl]-methyl-amino}-acetic acid;

{Methyl-[3-[3-(4-methyl-benzoyl)-phenoxy]-3-(3-trifluoromethyl-phenyl)-propyl]-amino}-acetic acid;

{[3-[3-(4-Methoxy-benzoyl)-phenoxy]-3-(3-trifluoromethyl-phenyl)-propyl]-methyl-amino}-acetic acid;

{[3-[3-(4-Chloro-benzoyl)-phenoxy]-3-(3-trifluoromethyl-phenyl)-propyl]-methyl-amino}-acetic acid; and {Methyl-[3-[3-(5-methyl-thiazole-2-carbonyl)-phenoxy]-3-(3-trifluoromethyl-phenyl)-propyl]-amino}-acetic acid;

and the pharmaceutically acceptable salts of such compounds.

This invention also relates to a method of treating a disorder or condition selected from mood disorders, such as depression, or more particularly, depressive disorders, for example, single episodic or recurrent major depressive disorders, dysthymic disorders, depressive neurosis and neurotic depression, melancholic depression, including anorexia, weight loss, insomnia, early morning waking and psychomotor retardation, atypical depression (or reactive depression), including increased appetite, hypersomnia, psychomotor agitation or irritability, seasonal affective disorder and pediatric depression; or bipolar disorders or manic depression, for example, bipolar I disorder, bipolar II disorder and cyclothymic disorder; conduct disorder and disruptive behavior disorder; anxiety disorders, such as panic disorder with or without agoraphobia, agoraphobia without history of panic disorder, specific phobias, for example, specific animal phobias, social anxiety, social phobia, obsessive-compulsive disorder, stress disorders, including post-traumatic stress disorder and acute stress disorder, and generalized anxiety disorders; borderline personality disorder; psychosis, schizophrenia, conduct disorder, disruptive behavior disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia, HIV-1 associated dementia, AIDS dementia complex (ADC), HIV encephalopathy and senile dementia of the Alzheimer's type) and memory disorders in a mammal, including a human, comprising administering to a mammal in need of such treatment an amount of a compound of the formula I, or a pharmaceutically acceptable salt thereof, that is effective in treating such condition or disorder.

This invention also relates to a pharmaceutical composition for treating a disorder or condition selected from mood disorders, such as depression, or more particularly, depressive disorders, for example, single episodic or recurrent major depressive disorders, dysthymic disorders, depressive neurosis and neurotic depression, melancholic depression, including anorexia, weight loss, insomnia, early morning waking and psychomotor retardation, atypical depression (or reactive depression), including increased appetite, hypersomnia, psychomotor agitation or irritability, seasonal affective disorder and pediatric depression; or bipolar disorders or manic depression, for example, bipolar I disorder, bipolar II disorder and cyclothymic disorder; conduct disorder and disruptive behavior disorder; anxiety disorders, such as panic disorder with or without agoraphobia, agoraphobia without history of panic disorder, specific phobias, for example, specific animal phobias, social anxiety, social phobia, obsessive-compulsive disorder, stress disorders, including post-traumatic stress disorder and acute stress disorder, and generalized anxiety disorders; borderline personality disorder; psychosis, schizophrenia, conduct disorder, disruptive behavior disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia, HIV-1 associated dementia, AIDS dementia complex (ADC), HIV encephalopathy and senile dementia of the Alzheimer's type) and memory disorders in a mammal, including a human, comprising administering to a mammal in need of such treatment an amount of a compound of the formula I, or a pharmaceutically acceptable salt thereof, that is effective in treating such disorder or condition.

This invention also relates to a method of treating a disorder or condition selected from mood disorders, such as depression, or more particularly, depressive disorders, for example, single episodic or recurrent major depressive disorders, dysthymic disorders, depressive neurosis and neurotic depression, melancholic depression, including anorexia, weight loss, insomnia, early morning waking and psychomotor retardation, atypical depression (or reactive depression), including increased appetite, hypersomnia, psychomotor agitation or irritability, seasonal affective disorder and pediatric depression; or bipolar disorders or manic depression, for example, bipolar I disorder, bipolar II disorder and cyclothymic disorder; conduct disorder and disruptive behavior disorder; anxiety disorders, such as panic disorder with or without agoraphobia, agoraphobia without history of panic disorder, specific phobias, for example, specific animal phobias, social anxiety, social phobia, obsessive-compulsive disorder, stress disorders, including post-traumatic stress disorder and acute stress disorder, and generalized anxiety disorders; borderline personality disorder; psychosis, schizophrenia, conduct disorder, disruptive behavior disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder;

movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia, HIV-1 associated dementia, AIDS dementia complex (ADC), HIV encephalopathy and senile dementia of the Alzheimer's type) and memory disorders in a mammal, including a human, comprising administering to a mammal in need of such treatment a glycine transport inhibiting amount of a compound of the formula I, or a pharmaceutically acceptable salt thereof.

This invention also relates to a pharmaceutical composition for treating a disorder or condition selected from mood disorders, such as depression, or more particularly, depressive disorders, for example, single episodic or recurrent major depressive disorders, dysthymic disorders, depressive neurosis and neurotic depression, melancholic depression, including anorexia, weight loss, insomnia, early morning waking and psychomotor retardation, atypical depression (or reactive depression), including increased appetite, hypersomnia, psychomotor agitation or irritability, seasonal affective disorder and pediatric depression; or bipolar disorders or manic depression, for example, bipolar I disorder, bipolar II disorder and cyclothymic disorder; conduct disorder and disruptive behavior disorder; anxiety disorders, such as panic disorder with or without agoraphobia, agoraphobia without history of panic disorder, specific phobias, for example, specific animal phobias, social anxiety, social phobia, obsessive-compulsive disorder, stress disorders, including post-traumatic stress disorder and acute stress disorder, and generalized anxiety disorders; borderline personality disorder; psychosis, schizophrenia, conduct disorder, disruptive behavior disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia, HIV-1 associated dementia, AIDS dementia complex (ADC), HIV encephalopathy and senile dementia of the Alzheimer's type) and memory disorders in a mammal, including a human, comprising administering to a mammal in need of such treatment a glycine transport inhibiting amount of a compound of the formula I, or a pharmaceutically acceptable salt thereof.

The term "alkyl", as used herein, unless otherwise indicated, includes saturated monovalent hydrocarbon radicals having straight, branched or cyclic moieties or combinations thereof. Examples of "alkyl" groups include, but are not limited to, methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like.

The term "halo", as used herein, means chloro, fluoro, iodo or bromo.

The term "alkoxy", as used herein, means "alkyl-O-", wherein "alkyl" is defined as above.

The term "treating", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

The compounds of formula I may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

The present invention also includes isotopically labelled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

DETAILED DESCRIPTION OF THE INVENTION

The compounds of the formula (I) of this invention may be prepared as described in the following reaction schemes.

Unless otherwise indicated, in the reaction schemes and discussion that follow, ring A, Y and X are defined as above.

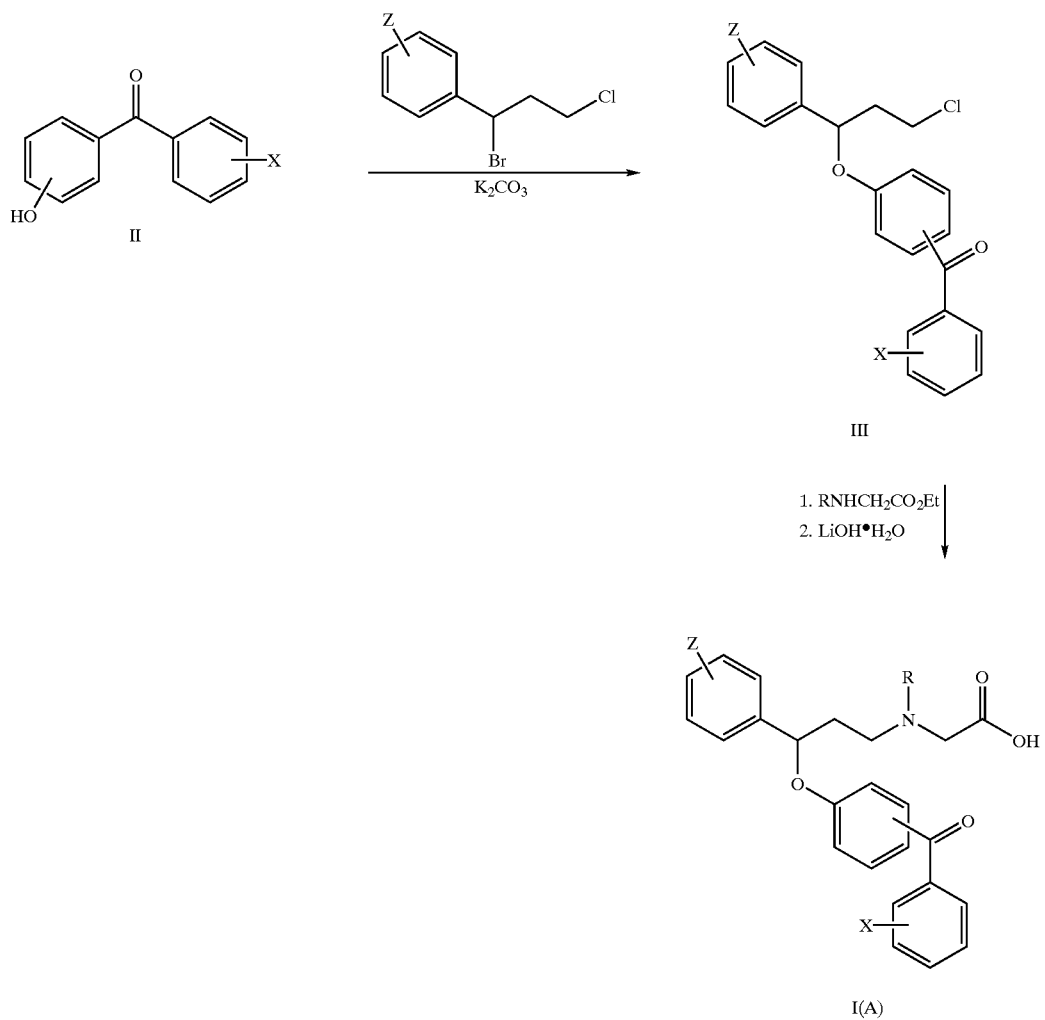
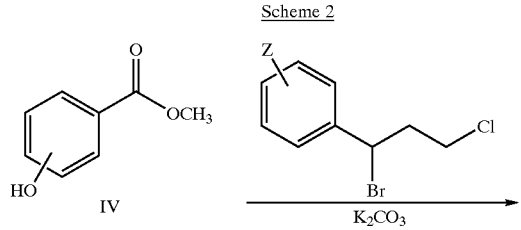
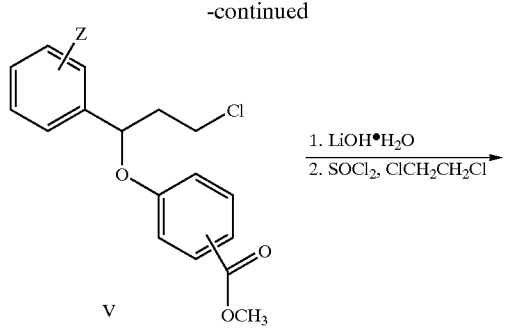

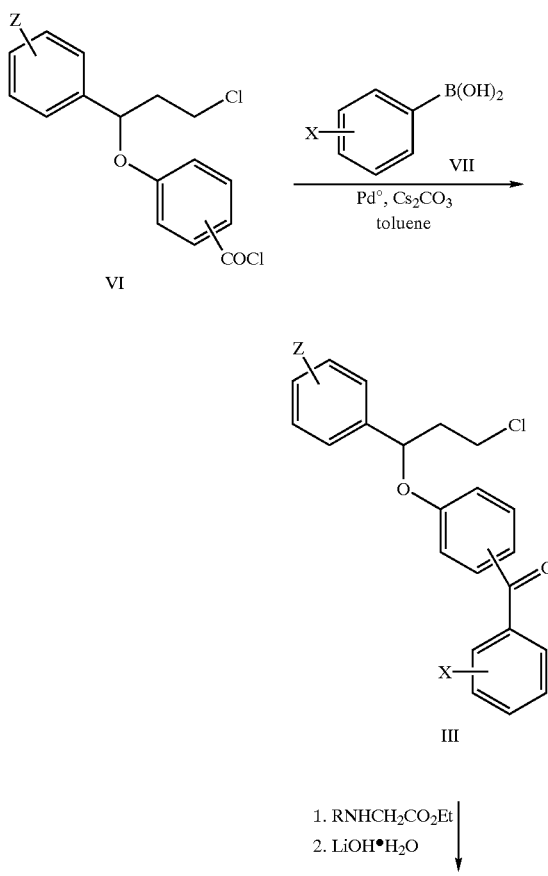
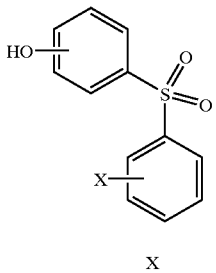
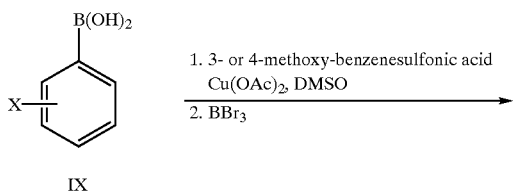

Schemes 1, 2 and 3 illustrate methods of preparing compounds of the formula I wherein ring A is phenyl. Methods analogous to these can be used to prepare compounds of the formula I wherein ring A is other than phenyl. Such methods will be obvious to those of skill in the art.

Schemes 1 and 2 illustrate methods of preparing compounds of the formula I wherein Y is C=O. Compounds of the formula I wherein Y is $SO_2$ can be prepared using the procedure illustrated in Scheme 1 and described below, but replacing the starting material of formula 11 with a compound of the formula X, the synthesis of which is illustrated in Scheme 3.

Referring to Scheme 1, a compound of the formula II, wherein the hydroxy group is attached at the meta or para position, is reacted with 1-bromo-3-chloro-propylbenzene in the presence of an alkali metal or alkaline earth metal carbonate or bicarbonate to form the corresponding compound of formula III wherein the phenylcarbonyl group is attached at the meta or para position. This reaction is typically conducted in a reaction inert solvent such as acetone, methyl isobutyl ketone (MIBK), methyl ethyl ketone (MEK) or acetonitrile, at a temperature from about room temperature to about the reflux temperature of the solvent, preferably at about the reflux temperature. The resulting compound of formula III is then converted into the corresponding compound of formula I by the following two step procedure.

First, the compound of formula III is alkylated by reacting it with methyl glycine ethyl ester (sacrosine ethyl ester) in a reaction inert solvent such as dimethyl formamide (DMF), methyl pyrrolidone or dimethylacetamide, at a temperature from about room temperature to about the reflux temperature of the solvent, preferably at about 90° C. Then, the resulting ester is hydrolyzed using lithium hydroxide in water, a mixture of water, an alcohol containing one to four carbons and/or an ethereal solvent such as tetrahydrofuran to form the corresponding carboxylic acid of formula I wherein the phenylcarbonyl is attached at the meta or para position. The hydrolysis reaction can be carried out in situ or after isolating the ester from the alkylation reaction. In either case, the hydrolysis is carried out using the same or similar solvent as that used in the alkylation reaction and is carried out under the same or similar conditions.

Scheme 2 illustrates an alternate method of preparing compounds of the formula I. Referring to Scheme 2, the compound of formula IV, wherein the hydroxy group is attached at the meta or para position, is reacted with 1-bromo-3-chloro-propylbenzene, wherein the benzene ring is substituted with Z and Z is defined as above, using the procedure described above for preparing compounds of the formula III. The resulting ester of formula V, wherein the methoxycarbonyl group is attached at the meta or para position, is then hydrolyzed using lithium hydroxide in water, a mixture of water, an alcohol containing one to four carbons and/or an ethereal solvent such as tetrahydrofuran, as described above, to form the corresponding carboxylic acid. Reaction of the carboxylic acid with sulfonyl chloride in methylene chloride yields the corresponding acid chloride of formula VI, wherein the COCl group is attached at the meta or para position. This reaction can be conducted in situ or after isolating the acid product of the hydrolysis reaction. Typically, the reaction is carried out by refluxing the acid with thionyl chloride, usually in excess, in a hydrocarbon or chlorohydrocarbon solvent such as methylene chloride, chloroform or carbon tetrachloride, for a period of about one to about 24 hours, followed by evaporation to remove the solvent and excess reagent before conducting the following reaction.

The acid chloride of formula VI can be converted into the corresponding compound of formula III, wherein the phenylcarbonyl group is attached at the meta or para position, by reacting it with the appropriate boronic acid derivative of formula VII in the presence of triphenylphosphine palladium or another palladium(0) source, preferably triphenylphosphine palladium, and cesium or potassium carbonate under Suzuki reaction conditions. This reaction can be carried out at temperatures ranging from about 0° C to about the reflux temperature of the solvent, and is preferably carried out at about 100° C. Suitable solvents include toluene, benzene, toluene, dimethoxyethane and tetrahydrofuran (THF). Toluene is preferred.

Alkylation of the compound of formula III using methyl glycine ethyl ester (sacrosine ethyl ester), as described above for the formation of compounds of the formula I from compounds of the formula III, following by hydrolysis of the resulting ester using lithium hydroxide hydroxide in water, a mixture of water, an alcohol containing one to four carbons and/or an ethereal solvent such as tetrahydrofuran, also as described above, yields the desired carboxylic acid of formula I wherein the phenylcarbonyl group is attached at the meta or para position.

Referring to Scheme 3, a mixture of 3- or 4-methoxybenzenesulfinic acid, a compound of the formula IX, an organic base such as triethylamine or diisopropylethylamine, preferably triethylamine, cupric acetate, molecular sieves, and DMSO is stirred under a stream of air for a period from about 1 hour to about 36 hours, at a temperature from about 25° C. to about 100° C. This reaction, which produces 3- or 4-methoxyphenylsulfone, is preferably carried out at about 25° C. The resulting 3- or 4-methoxyphenylsulfone is then reacted with $BBr_3$ in methylene chloride at a temperature from about room temperature to about −70° C. for about 1 hour to about 24 hours, to yield a compound of the formula X wherein the hydroxy group is attached at the meta or para position.

The resulting compound of formula X can be converted into the corresponding compound of formula I by a method analogous to that illustrated in Scheme 1 and discussed above for converting compounds of the formula 11 into compounds of the formula I.

The compounds of formula I and the intermediates shown in the above reaction schemes can be isolated and purified by conventional procedures, such as recrystallization or chromatographic separation.

In so far as the compounds of formula (I) of this invention can contain basic substituents, they are capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained.

The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, ptoluenesulfonate and pamoate (i.e., 1,1'-methylene-bis-(2-hydroxy-3-naphthoate))salts.

All compounds of the invention have an acidic group and are capable of forming base salts with various pharmaceutically acceptable cations. Examples of such salts include the alkali metal or alkaline-earth metal salts and, particularly, the sodium and potassium salts. These salts are all prepared by conventional techniques.

The chemical bases which are used as reagents to prepare the pharmaceutically acceptable base salts of this invention are those which form non-toxic base salts with the herein described acidic derivatives. These particular non-toxic base salts include those derived form such pharmaceutically acceptable cations as sodium, potassium, calcium and magnesium, etc. These salts can easily be prepared by treating the aforementioned acidic compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The active compounds of the present invention exhibit significant glycine transport inhibiting activity and therefore are of value in the treatment of a wide variety of clinical conditions that are characterized by the deficit of glutamateric neurotransmission in mammalian subjects, especially humans. Such conditions include the positive and negative symptoms of schizophrenia and other psychoses, and cognitive deficits.

The active compounds of the formula (I) of this invention can be administered via either the oral, parenteral (such as subcutaneous, intraveneous, intramuscular, intrasternal and infusion techniques), rectal, intranasal or topical routes to mammals. In general, these compounds are most desirably administered to humans in doses ranging from about 1 mg to about 2000 mg per day, although variations will necessarily occur depending upon the weight and condition of the subject being treated and the particular route of administration chosen. However, a dosage level that is in the range of from about 0.1 mg to about 20 mg per kg of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of the present invention were assayed for their activity in inhibiting glycine reuptake in synaptosomes by first preparing synaptosomes and then measuring neurotransmitter reuptake activity as follows:

Male Sprague Dawley rats were decapitated and the brains removed. The whole brains were dissected out and placed in ice cold sucrose buffer; 1 gram in 20 mls (320 mM sucrose containing 1 mg/ml glucose, 0.1 mM EDTA and brought up to pH 7.4 with Tris base). The tissue was homogenized in a glass homogenizing tube with a teflon pestle at 350 RPMS using a Potters homogenizer. The homogenate was centrifuged at 1000× g for 10 min at 4° C. The resulting supernatant was recentrifuged at 17,000× g for 20 min at 4° C. The final pellet was resuspended in an appropriate volume of sucrose buffer containing 5 mM alanine, to yield less than 10% uptake.

The uptake assays were conducted in 96 well matrix plates. Each well contained 25 µL of solvent, inhibitor or 10 mM glycine for nonspecific uptake, 200 µL of [$^3$H]-glycine (40 nM final), made up in modified Krebs containing 5 mM alanine and glucose (1 mg/ml) and 25 µL of synaptosomes. The plates were then incubated at room temperature for the 15 min. The incubation was terminated by filtration through GF/B filters, using a 96 well Brandel Cell Harvester. The filters were washed with modified Krebs buffer and either counted in a liquid scintillation counter or in a LKB Beta Plate counter.

The present invention is illustrated by the following examples. However, it should be understood that the invention is not limited to the specific details of these examples. Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in CDCl$_3$ by a JEOL NMR spectrometer (JNM-GX270, 270MHz for $^1$H, 67.5 MHz for $^{13}$C) unless otherwise indicated and peak positions are expressed in parts per million (ppm) downfield from tetramethylsilane. The peak shapes are denoted as follows: s, singlet; d, doublet; t, triplet; m, multiplet; br, broad.

EXAMPLE 1

{[3-(4-benzoyl-phenoxy)-3-phenyl-propyl]-methyl-amino}-acetic Acid

A. [4-(3-Chloro-1-phenyl-propoxy)-phenyl]-phenyl-methanone:

(Referring to Scheme 1) To a 125 mL round-bottomed flask equipped with condenser and N$_2$ inlet were added 3.78 g (16.15 mmol) 3-chloro-1-bromo-1-phenylpropane, 3.52 g (17.76 mmol) 4-benzoylphenol, 4.46 g (32.3 mmol) potassium carbonate, and 27 mL methylisobutylketone. The reaction was refluxed 40 hours (h), cooled, and poured into water. After extracting with ethyl acetate, the organic layer was washed with brine, dried over sodium sulfate, and evaporated. The residue was chromatographed on silica gel using ethyl acetate/hexane as eluant to afford 3.0 g (53%) of an oil.

$^1$H-NMR (δ, CDCl3): 2.38 (AB, 2H), 3.73 (AB, 2H), 5.48 (dd, J=4,8, 1 H), 6.92 (m, 2H), 7.2–7.8 (m, 12H).

$^{13}$C-NMR (δ, CDCl3): 41.04, 41.13, 76.83, 115.28, 125.76, 126.53, 128.11, 128.41, 128.87, 129.61, 131.80, 133.54, 138.24, 139.96, 161.43, 195.34.

B. {[3-(4-Benzoyl-phenoxy)-3-phenyl-propyl]-methyl-amino}-acetic Acid Ethyl Ester:

To a 125 mL round-bottomed flask equipped with condenser and $N_2$ (nitrogen) inlet were added 701 mg (2.0 mmol) [4-(3-chloro-1-phenyl-propoxy)-phenyl]-phenyl-methanone, 307 mg (2.0 mmol) sarcosine ethyl ester hydrochloride, 0.697 mL (4.0 mmol) diisopropylethylamine, and 5 mL dry N-methylpyrrolidinone. The reaction was heated at 90–95° C. for 50 hours (h), cooled, and poured into water. After extracting with ethyl acetate, the organic layer was washed with water (3 times) and brine, dried over sodium sulfate, and evaporated. The residue was chromatographed on silica gel using methylene chloride/methanol as eluant to afford 350 mg (41%) of an oil.

$^1$H-NMR ($\delta$, CDCl3): 1.20 (t, J=6, 3H), 2.08 (AB, 2H), 2.36 (s, 3H), 2.665 (m, 2H), 3.22 (s, 2H), 4.11 (q, J=6, 2H), 5.36 (dd, J=3,8, 1H), 6.89 (m, 2H), 7.2–7.7 (m, 12H).

$^{13}$C-NMR ($\delta$, CDCl3): 14.19, 36.63, 42.30, 53.04, 53.20, 58.65, 58.93, 60.40, 78.25, 115.29, 125.78, 127.67, 127.93, 128.22, 128.89, 129.52, 131.66, 132.50, 138.21, 141.16, 161.91, 170.88, 195.37.

MS (%): 432 (parent+1, 100).

C. {[3-(4-Benzoyl-phenoxy)-3-phenyl-propyl]-methyl-amino}-acetic Acid:

To a 125 mL round-bottomed flask equipped with N2 inlet were added the above ester dissolved in 6 mL tetrahydrofuran, followed by a solution of 200 mg lithium hydroxide hydrate in 10 mL water with sufficient methanol to give a solution. The reaction was stirred at room temperature for 1 hour, evaporated, and taken up in 5 mL water. The pH was adjusted to 1 with 6 N hydrochloric acid, and the aqueous layer extracted twice with methylene chloride. The organic layer was dried over sodium sulfate and evaporated to an oil, which solidified on standing under high vacuum to an amorphous solid, 82 mg (9.3%)

$^1$H-NMR ($\delta$, CDCl3): 2.40 (m, 2H), 2.89 (s, 3H), 3.41 (m, 2H), 4.07 (m, 2H), 5.48 (m, 1H), 6.82 (m, 2H), 7.1–7.6 (m, 12H).

$^{13}$C-NMR ($\delta$, CDCl3): 33.07, 41.38, 48.93, 54.29, 67.95, 104.43, 112.49, 115.55, 122.58, 126.01, 128.11, 128.37, 129.16, 129.61, 129.87, 130.38, 130.44, 132.16, 132.42, 137.70, 139.35, 160.88, 166.58, 195.68.

MS (%): 404 (parent+1) for APCl positive and 402 (parent-1) for APCl negative.

Anal. Calc'd. for $C_{25}H_{25}NO_4 \cdot HCl \cdot \frac{1}{2}(CH_2Cl_2) \cdot \frac{1}{2}H_2O$: C 62.33, H 5.74, N 2.85. Found: C 62.47, H 5.56, N 2.74.

EXAMPLE 2

(Methyl-{3-[4-(naphthalene-2-carbonyl)-phenoxy]-3-phenyl-propyl}-amino)-acetic Acid Prepared as in Example 1 using 4-naphthoylphenol as starting material, with an overall yield for 4 steps of 4%, mp 77–89° C.

$^1$H-NMR ($\delta$, CDCl3): 2.39 (m, 2H), 2.87 (s, 3H), 3.45 (m, 2H), 3.885 (m, 2H), 5.46 (m, 1H), 6.83 (m, 2H), 7.1–7.8 (m, 12H), 8.05 (s, 1H).

$^{13}$C-NMR ($\delta$, CDCl3): 33.36, 41.66, 53.71, 54.14, 56.75, 115.78, 125.90, 126.04, 126.97, 127.96, 128.36, 128.40, 128.56, 129.23, 129.48, 130.98, 131.41, 132.37, 132.53, 135.20, 135.24, 139.71, 161.12, 167.88, 195.61

MS (%): 454 (parent+1) and 460 (parent+Li) at APCl positive, 452 (parent-1) at APCl negative Anal. Calc'd for $C_{29}H_{27}NO_4 \cdot HCl \cdot (CH_2Cl_2)$: C 62.67, H 5.26, N 2.44. Found: C 63.00, H 5.48, N 2.46.

EXAMPLE 3

(Methyl-{3-[4-(4-methyl-benzoyl)-phenoxy]-3-phenyl-propyl}-amino)-acetic Acid

A. 4-(3-Chloro-1-phenyl-propoxy)-benzoic Acid Methyl Ester:

(Referring to Scheme 2) Prepared as in Example 1A, using 4-(carbomethoxy)-phenol, in 71% yield, as an oil.

$^1$H-NMR ($\delta$, CDCl3): 2.37 (AB, 2H), 3.67 (AB, 2H), 3.815 (s, 3H), 5.44 (dd, J=5,8, 1H), 6.86 (m, 2H), 7.1–7.3 (m, 5H), 7.87 (m, 2H).

$^{13}$C-NMR ($\delta$, CDCl3): 41.33, 41.40, 52.03, 77.04, 115.66, 122.97, 126.06, 128.31, 128.36, 129.14, 131.70, 140.25, 161.81, 167.04.

This material was hydrolyzed as in Example 1C to provide 4-(3-chloro-1-phenyl-propoxy)-benzoic acid in 62% overall yield, which was used in the next step.

B. 4-(3-Chloro-1-phenyl-propoxy)-benzoyl Chloride:

To a 125 mL round-bottomed flask equipped with condenser and N2 inlet were added 1.0 g (3.44 mmol) 4-(3-chloro-1-phenyl-propoxy)-benzoic acid, 20 mL 1,2-dichloroethane, and 0.3 mL (4.13 mmol) thionyl chloride. The solution was refluxed for 2 hours, evaporated, and the acid chloride used directly in the next step.

C. [4-(3-Chloro-1-phenyl-propoxy)-phenyl]-p-tolyl-methanone:

To a 125 mL round-bottomed flask equipped with condenser and N2 inlet were added 1.06 g (3.44 mmol) 4-(3-chloro-1-phenyl-propoxy)-benzoyl chloride, 468 mg (3.44 mmol) p-tolyl boronic acid, 2.24 g (6.88 mmol) cesium carbonate, 40 mg (0.034 mmol) tetrakistriphenylphosphine palladium, and 25 mL dry toluene. The reaction was heated to 100° C. for 18 h, cooled, and poured into water. After extracting with ethyl acetate, the organic layer was washed with brine, dried over sodium sulfate, and evaporated. The residue was chromatographed on silica gel using ethyl acetate/hexane as eluant to afford 480 mg (38%) of an oil.

$^1$H-NMR ($\delta$, CDCl3): 2.35 (AB, 2H), 2.37 (s, 3H), 3.65 (AB, 2H), 5.48 (dd, J=5,8, 1H), 6.91 (m, 2H), 7.1–7.4 (m, 7H), 7.62 (m, 2H), 7.69 (m, 2H).

$^{13}$C-NMR ($\delta$, CDCl3): 21.82, 41.36, 41.44, 77.13, 115.56, 126.09, 128.40, 129.09, 129.18, 130.20, 132.51, 132.67, 135.62, 140.32, 142.81, 161.56, 195.33.

D. (Methyl-{3-[4-(4-methyl-benzoyl)-phenoxy]-3-phenyl-propyl}-amino)-acetic Acid Ethyl Ester:

Prepared as in Example 1 B in 25.5% yield as an oil.

$^1$H-NMR ($\delta$, CDCl3): 1.205 (t, J=6, 3H), 2.09 (AB, 2H), 2.365 (s, 3H), 2.67 (m, 2H), 3.225 (s, 2H), 4.11 (q, J=6, 2H), 5.34 (dd, J=5,8, 1H), 6.87 (m, 2H), 7.1–7.4 (m, 7H), 7.58 (m, 2H), 7.65 (m, 2H).

$^{13}$C-NMR ($\delta$, CDCl3): 14.48, 21.79, 36.83, 42.50, 53.28, 58.83, 60.66, 78.39, 115.51, 126.12, 128.00, 128.94, 129.01, 130.15, 130.54, 132.45, 135.67, 141.38, 142.70, 161.92, 171.05, 195.43.

MS (%): 446 (parent+1, 100).

E. (Methyl-{3-[4-(4-methyl-benzoyl)-phenoxy]-3-phenyl-propyl}-amino)-acetic Acid:

Prepared as in Example 1C in 19% overall yield, mp 85–95° C.

$^1$H-NMR ($\delta$, CDCl3): 2.34 (s, 3H), 2.35 (m, 2H), 2.86 (s, 3H), 3.43 (m, 2H), 3.95 (m, 2H), 5.46 (m, 1 H), 6.81 (m, 2H), 7.1–7.3 (m, 7H), 7.5–7.6 (m, 4H).

$^{13}$C-NMR ($\delta$, CDCl3): 21.80, 33.20, 41.69, 54.33, 56.42, 73.64, 115.71, 126.06, 128.54, 129.11, 129.22, 130.20, 131.07, 132.33, 135.24, 139.68, 143.08, 160.92, 167.32, 195.49.

MS (%): 418 (parent+1) and 416 (parent−1) at APCl negative Anal. Calc'd for $C_{26}H_{27}NO_4·HCl·\frac{3}{2}(H_2O)$: C 64.93, H 6.50, N 2.91. Found: C 64.98, H 6.32, N 2.99.

EXAMPLE 4

(Methyl-{3-[4-(4-methoxy-benzoyl)-phenoxy]-3-phenyl-propyl}-amino)-acetic Acid

Prepared as in Example 3, as an amorphous solid in 29% yield.

$^1$H-NMR (δ, CDCl3): 2.40 (m, 2H), 2.875 (s, 3H), 3.40 (m, 2H), 3.77 (s, 3H), 4.01 (m, 2H), 5.46 (m, 1 H), 6.82 (m, 4H), 7.1–7.7 (m, 9H).

$^{13}$C-NMR (δ, CDCl3): 33.38, 41.96, 53.72, 54.50, 55.68, 68.34, 113.71, 115.75, 126.10, 128.54, 129.22, 130.38, 131.29, 132.12, 132.49, 139.75, 143.54, 160.77, 163.19, 194.67.

MS (%): 434 (parent+1) and 440 (parent+Li) at APCl positive, 432 (parent−1) at APCl negative Anal. Calc'd for $C_{26}H_{27}NO_5·HCl·(CH_2Cl_2)$: C 58.44, H 5.45, N 2.52. Found: C 58.24, H 5.81, N 2.34.

EXAMPLE 5

(Methyl-{3-[4-(4-chloro-benzoyl)-phenoxy]-3-phenyl-propyl}-amino)-acetic Acid

Prepared as in Example 3, as an amorphous solid in 30% yield.

$^1$H-NMR (δ, CDCl3): 2.37 (m, 2H), 2.85 (s, 3H), 3.42 (s, 2H), 3.78 (m, 2H), 5.44 (m, 1H), 6.83 (m, 2H), 7.1–7.7 (m, 11H).

$^{13}$C-NMR (δ, CDCl3): 33.41, 41.60, 53.70, 53.95, 56.93, 77.64, 115.80, 125.99, 126.91, 128.67, 128.73, 128.73, 129.26, 130.39, 130.66, 131.11, 131.34, 132.39, 136.32, 138.61, 139.60, 143.70, 161.23, 168.05, 194.29.

MS (%): 438 (parent+1) and 444 (parent+Li) at APCl positive, 436 (parent−1) at APCl negative.

Anal. Calc'd for $C_{25}H_{24}NO_4Cl·HCl·\frac{1}{2}(CH_2Cl_2)$: C 59.26, H 5.07, N 2.71. Found: C 58.85, H 4.90, N 2.16.

EXAMPLE 6

(Methyl-{3-[4-(2-methoxy-benzoyl)-phenoxy]-3-phenyl-propyl}-amino)-acetic Acid

Prepared as in Example 3, as an amorphous solid in 21% yield.

$^1$H-NMR (δ, CDCl3): 2.36 (m, 2H), 2.84 (s, 3H), 3.43 (m, 2H), 3.57 (s, 3H), 3.93 (m, 2H), 5.42 (m, 1H), 6.76 (m, 2H), 6.9–7.0 (m, 2H), 7.1–7.4 (m, 7H), 7.54 (m, 2H).

$^{13}$C-NMR (δ, CDCl3): 33.24, 41.78, 53.71, 54.35, 55.80, 73.28, 111.63, 115.71, 120.63, 126.03, 128.53, 128.99, 129.06, 129.19, 129.33, 131.13, 131.79, 132.29, 139.58, 157.12, 161.48, 167.17, 195.25.

MS (%): 434 (parent+1) and 440 (parent+Li) at APCl positive, 432 (parent−1) at APCl negative.

Anal. Calc'd for $C_{26}H_{27}NO_5·HCl·\frac{3}{4}(CH_2Cl_2)$: C 60.21, H 5.57, N 2.62. Found: C 59.84, H 5.62, N 2.18.

EXAMPLE 7

(Methyl-{3-[4-(3,4-dichloro-benzoyl)-phenoxy]-3-phenyl-propyl}-amino)-acetic Acid Prepared as in Example 3, as an amorphous solid in 31% yield.

$^1$H-NMR (δ, CDCl3): 2.47 (m, 2H), 2.99 (s, 3H), 3.55 (m, 2H), 4.01 (m, 2H), 5.52 (m, 1H), 6.89 (m, 2H), 7.2–7.8 (m, 10H).

$^{13}$C-NMR (δ, CDCl3): 33.56, 41.37, 53.39, 53.68, 73.79, 115.87, 125.98, 128.38, 129.33, 130.46, 131.13, 132.50, 136.74, 138.34, 141.53, 143.56, 161.42, 167.03, 193.51.

Anal. Calc'd for $C_{25}H_{23}NO_4Cl_2·HCl·H_2O$: C 57.00, H 4.97, N 2.66. Found: C 57.01, H 4.74, N 1.97.

EXAMPLE 8

(Methyl-{3-[4-(3-trifluoromethyl-benzoyl)-phenoxy]-3-phenyl-propyl}-amino)-acetic Acid Prepared as in Example 3, as an amorphous solid in 19% yield.

$^1$H-NMR (δ, CDCl3): 2.41 (m, 2H), 2.89 (s, 3H), 3.49 (m, 2H), 3.97 (m, 2H), 5.47 (m, 1H), 6.85 (m, 2H), 7.1–7.8 (m, 10H), 7.87 (s, 1H).

$^{13}$C-NMR (δ, CDCl3): 36.81, 42.49, 53.24, 58.84, 78.53, 115.83, 124 (J=1000 Hz), 126.09, 128.08, 129.00, 129.36, 131.00 (quartet, J=100 Hz), 132.61, 132.96, 139.15, 141.18, 162.57, 171.07, 194.09.

MS (%): 472 (parent+1) and 470 (parent−1) at APCl negative

Anal. Calc'd for $C_{26}H_{24}NO_4F_3·HCl·\frac{1}{2}H_2O$: C 60.41, H 5.07, N 2.71. Found: C 60.20, H 5.12, N 2.50.

EXAMPLE 9

{[3-(4-Benzenesulfonyl-phenoxy)-3-phenyl-propyl]-methyl-amino}acetic Acid

Prepared as in Example 1 using 4-benzenesulfonylphenol as starting material, in 13% yield, as a solid, mp 95–100° C.

$^{13}$C-NMR (δ, CDCl3): 33.17, 41.58, 53.75, 54.09, 56.54, 77.58, 116.75, 126.05, 127.49, 128.63, 129.23, 129.49, 129.81, 133.26, 133.52, 139.36, 141.95, 161.45, 167.55.

MS (%): 440 (parent+1) and 438 (parent−1) at APCl negative

Anal. Calc'd. for $C_{24}H_{25}NO_5S·HCl·\frac{1}{2}H_2O$: C 59.44, H 5.61, N 2.89. Found: C 59.13, H 5.43, N 2.81.

EXAMPLE 10

(Methyl-{3-phenyl-3-[4-(toluene-4-sulfonyl)-phenoxy]-propyl}amino)-acetic Acid

Prepared as in Example 9 in 33% yield as an amorphous solid.

$^{13}$C-NMR (δ, CDCl3): 21.71, 32.99, 41.65, 53.75, 54.26, 56.02, 116.72, 126.08, 127.54, 128.62, 129.22, 129.61, 130.11, 133.93, 139.00, 139.36, 144.21, 161.29, 167.05.

MS (%): 454 (parent+1) and 460 (parent+Li) at APCl positive, 452 (parent−1) at APCl negative.

Anal. Calc'd. for $C_{25}H_{27}NO_5S·HCl·\frac{3}{2}H_2O$: C 58.08, H 6.04, N 2.71. Found: C 57.82, H 5.73, N 2.66.

EXAMPLE 11

({3-[4-(4-Methoxy-benzenesulfonyl)-phenoxy]-3-phenyl-propyl}methyl-amino)-acetic Acid Prepared as in Example 9 in 25% yield as an amorphous solid.

$^{13}$C-NMR (δ, CDCl3): 31.53, 41.61, 53.66, 54.34, 55.87, 59.53, 114.70, 116.73, 126.08, 128.62, 129.24, 129.42, 129.74, 131.10, 133.47, 134.33, 134.49, 138.78, 161.21, 163.41, 166.60.

MS (%): 470 (parent+1) and 476 (parent+Li) at APCl positive.

Anal. Calc'd. for $C_{25}H_{27}NO_6S·HCl·\frac{3}{2}H_2O$: C 56.33, H 5.86, N 2.63. Found: C 56.20, H 6.05, N 2.81.

EXAMPLE 12

({3-[4-(4-Chloro-benzenesulfonyl)-phenoxy]-3-phenyl-propyl]methyl-amino)-acetic Acid Prepared as in Example 9 in 22% yield as an amorphous solid.

$^{13}$C-NMR (δ, CDCl3): 33.17, 41.59, 53.72, 54.03, 56.64, 77.80, 116.87, 126.05, 128.67, 129.02, 129.25, 129.77, 129.85, 133.13, 139.30, 139.78, 140.50, 161.63, 167.68.

MS (%): 474/476 (parent+1 for $Cl^{35}/Cl^{37}$) at APCl positive.

Anal. Calc'd. for $C_{24}H_{24}NO_5SCl.HCl.\frac{1}{2}H_2O \frac{1}{2}(CH_2Cl_2)$: C 52.37, H 4.84, N 2.49. Found: C 52.34, H 4.95, N 2.54.

EXAMPLE 13

({3-[4-(4-Fluoro-benzenesulfonyl)-phenoxy]-3-phenyl-propyl}-methyl-amino)-acetic Acid Prepared as in Example 9 in 38% yield as an amorphous solid.

$^{13}$C-NMR (δ, CDCl3): 33.13, 41.68, 53.76, 54.25, 56.33, 116.66, 116.88, 126.06, 128.66, 129.23, 129.74, 130.30, 130.40, 133.37, 138.00, 139.26, 161.52, 164.13, 166.67, 167.02.

MS (%): 458 (parent+1) at APCl positive.

Anal. Calc'd. for $C_{24}H_{24}NO_5SF.HCl.2H_2O$: C 54.39, H 5.52, N 2.64. Found: C 54.42, H 5.28, N 2.83.

EXAMPLE 14

(Methyl-{3-[4-(naphthalene-1-sulfonyl)-phenoxy]-3-phenyl-propyl}amino)-acetic Acid:

Prepared as in Example 9, using 4-(1-napthylsulfonyl)phenol prepared as described below, in 23% yield as an amorphous solid.

$^{13}$C-NMR (δ, CDCl3): 38.91, 42.13, 54.61, 73.44, 116.75, 124.48, 124.62, 126.11, 127.13, 128.45, 128.68, 129.01, 129.28, 129.69, 129.84, 131.10, 134.36, 135.24, 136.25, 163.50, 166.81.

MS (%): 496 (parent+Li) at APCl positive.

Anal. Calc'd. for $C_{28}H_{27}NO_5S.HCl.2H_2O$: C 59.83, H 5.74, N 2.49. Found: C 59.77, H 6.26, N 2.52.

EXAMPLE 14A 4-(1-Napthylsulfonyl)phenol

A mixture of 344 mg (2.0 mmol) 4-methoxybenzene sulfinic acid, 688 mg (4.0 mmol) 1-naphthyl boronic acid, 1.39 mL (10.0 mmol) triethylamine, 363 mg (2.0 mmol) cupric acetate, 350 mg 4A molecular sieves, and 10 mL dry dimethylsulfoxide was stirred under a stream of air for 36 hours. The mixture was then poured into dilute aqueous hydrochloric acid, extracted into ethyl acetate, and the organic layer washed with water, aqueous sodium bicarbonate solution, and brine, dried over sodium sulfate, and evaporated. The residue was chromatographed on silica gel using ethyl acetate/hexane as eluant to afford 240 mg (40%) of 4-(1-napthylsulfonyl)phenol as an oil.

$^{13}$C-NMR (δ, CDCl$_3$): 55.80, 114.54, 124.58, 127.02, 128.45, 128.51, 129.22, 129.68, 129.88, 130.09, 133.42, 134.42, 135.07, 136.73, 138.56, 163.38.

EXAMPLE 15

(Methyl-{3-phenyl-3-[4-(4-trifluoromethylbenzenesulfonyl)phenoxy]-propyl}-amino)-acetic Acid Prepared as in Example 14 in 35% yield as an amorphous solid.

$^{13}$C-NMR (δ, CDCl3): 33.28, 41.66, 54.27, 70.28, 116.98, 126.03, 126.62, 128.12, 128.76, 129.28, 130.14, 132.46, 134.41 (q, J=12), 139.15, 145.55, 161.86, 166.80.

MS (%): 508 (parent+1) and 514 (parent+Li) at APCl positive.

EXAMPLE 16

(Methyl-{3-[4-(naphthalene-2-sulfonyl)-phenoxy]-3-phenyl-propyl}amino)-acetic Acid Prepared as in Example 14 in 22% yield as an amorphous solid.

$^{13}$C-NMR (δ, CDCl3): 33.20, 41.78, 54.29, 56.08, 116.82, 122.66, 126.04, 127.82, 128.09, 128.62, 128.81, 129.23, 129.55, 129.87, 132.31, 133.56, 135.03, 137.93, 138.77, 139.23, 161.39, 166.86.

MS (%): 490 (parent+1) and 496 (parent+Li) at APCl positive.

Anal. Calc'd. for $C_{28}H_{27}NO_5S.HCl.\frac{5}{2}H_2O$: C 58.89, H 5.82, N 2.45. Found: C 59.13, H 5.45, N 2.54.

EXAMPLE 17

({3-[4-(3-Methoxy-benzenesulfonyl)-phenoxy]-3-phenyl-propyl}methyl-amino)-acetic Acid Prepared as in Example 14 in 12% yield as a brown gum.

$^1$H-NMR (δ, CDCl$_3$): 2.01 (m, 2H), 2.36 (m, 2H), 2.835 (s, 3H), 3.38 (t, J=6, 2H), 3.78 (s, 3H), 4.2 (m, 2H), 5.3 (bs, 1H), 7.00 (m, 2H), 7.2–7.4 (m, 10H), 7.51 (m, 2H), 7.70 (m, 2H).

MS (%): 476 (parent+Li) at APCl positive, 468 (parent−1) at APCl negative

EXAMPLE 18

(Methyl-{3-phenyl-3-[4-(3-trifluoromethyl-benzenesulfonyl)phenoxy]-propyl}-amino)-acetic Acid Prepared as in Example 14 in 24% yield as an amorphous solid.

$^{13}$C-NMR (δ, CDCl3): 33.00, 41.80, 49.90, 54.35, 117.05, 121.95, 124.51, 124.66, 126.08, 127.38, 128.80, 129.34, 129.96, 130.15, 130.43, 131.01, 132.05 (q,.J=12), 139.14, 143.35, 161.91, 166.82.

MS (%): 508 (parent+1) and 514 (parent+Li) at APCl positive.

Anal. Calc'd. for $C_{25}H_{24}NO_5SF_3.HCl.\frac{1}{2}H_2O$: C 54.30, H 4.74, N 2.53. Found: C 53.97, H 5.38, N 2.89.

EXAMPLE 19

({3-[4-(2,4-Dichloro-benzenesulfonyl)-phenoxy]-3-phenyl-propyl}methyl-amino)-acetic Acid Prepared as in Example 14 in 13% yield as an amorphous solid.

$^{13}$C-NMR (δ, CDCl3) 35.37, 41.92, 55.82, 116.49, 126.05, 127.87, 128.82, 129.36, 130.97, 131.95, 133.86, 137.52, 140.56, 161.02, 162.13.

MS (%): 514/516 (parent+Li, $Cl^{35}/Cl^{37}$) at APCl positive.

EXAMPLE 20

({3-[4-(3,4-Dichloro-benzenesulfonyl)-phenoxy]-3-phenyl-propyl}-methyl-amino)-acetic Acid Prepared as in Example 14 in 15% yield as an amorphous solid.

$^{13}$C-NMR (δ, CDCl3): 33.36, 41.94, 53.66, 54.34, 76.78, 117.04, 126.06, 126.72, 128.78, 129.32, 129.42, 130.05, 131.62, 132.60, 134.04, 138.20, 139.07, 141.83, 143.44, 161.82, 166.74.

MS (%): 514/516 (parent+Li, $Cl^{35}/Cl^{37}$) at APCl positive.

Anal. Calc'd. for $C_{24}H_{23}NO_5SCl_2 \cdot HCl \cdot \frac{1}{2}H_2O$: C 52.04, H 4.55, N 2.53. Found: C 52.16, H 5.10, N 2.72.

EXAMPLE 21

(Methyl-{3-phenyl-3-[4-(thiophene-3-sulfonyl)-phenoxy]-propyl}-amino)-acetic Acid Prepared as in Example 14 in 10% yield as a foam.

$^{13}$C-NMR (δ, CDCl3): 30.85, 49.76, 53.95, 57.67, 76.11, 116.72, 125.91, 126.04, 128.58, 129.32, 129.69, 131.31, 139.20, 142.43, 161.45, 166.82.

MS (%): 452 (parent+Li) at APCl positive, 444 (parent−1) at APCl negative.

EXAMPLE 22

(Methyl-{3-[4-(3-methyl-benzoyl)-phenoxy]-3-phenyl-propyl}-amino)-acetic Acid

Prepared as in Example 3, as an amorphous solid in 25% yield.

$^{13}$C-NMR (δ, CDCl3): 21.53, 33.36, 41.64, 54.38, 56.50, 73.47, 115.73, 126.05, 127.22, 128.23, 128.56, 129.22, 130.32, 130.88, 132.45, 133.09, 138.02, 138.29, 139.64, 161.05, 167.20, 195.95.

MS (%): 418 (parent+1) and 416 (parent−1) at APCl negative Anal. Calc'd for $C_{26}H_{27}NO_4 \cdot HCl \cdot \frac{1}{2}H_2O \cdot \frac{1}{2}(CH_2Cl_2)$: C 62.97, H 5.98, N 2.77. Found: C 62.87, H 5.91, N 2.66.

EXAMPLE 23

{3-[4-(2,3-Dimethyl-benzoyl)-phenoxy]-3-phenyl-propyl}-methyl-amino)-acetic Acid Prepared as in Example 3, as an amorphous solid in 13% yield.

$^{13}$C-NMR (δ, CDCl3): 16.86, 20.33, 38.90, 44.43, 54.37, 56.30, 73.69, 115.80, 125.24, 125.42, 125.99, 129.26, 131.20, 131.37, 132.54, 134.26, 137.94, 139.73, 143.56, 161.59, 167.14, 198.18.

MS (%): 432 (parent+1) and 430 (parent−1) at APCl negative Anal. Calc'd for $C_{27}H_{29}NO_4 \cdot HCl \cdot \frac{1}{2}H_2O \cdot \frac{1}{2}(CH_2Cl_2)$: C 63.58, H 6.21, N 2.70. Found: C 63.40, H 6.17, N 2.55.

EXAMPLE 24

({3-[4-(3-Methoxy-benzoyl)-phenoxy]-3-phenyl-propyl}-methyl-amino)-acetic Acid

Prepared as in Example 3, as an amorphous solid in 5% yield.

$^{13}$C-NMR (δ, CDCl3): 30.57, 38.94, 45.38, 53.68, 55.68, 68.38, 114.49, 115.79, 118.56, 122.69, 126.09, 129.03, 129.31, 129.42, 131.13, 132.52, 132.66, 139.36, 159.70, 161.12, 166.81, 195.53.

Anal. Calc'd for $C_{26}H_{27}NO_5 \cdot HCl \cdot \frac{1}{2}H_2O$: C 65.20, H 6.10, N 2.92. Found: C 65.18, H 7.08, N 2.38.

EXAMPLE 25

(Methyl-{3-phenyl-3-[4-(4-trifluoromethyl-benzoyl)-phenoxy]-propyl}-amino)-acetic Acid Prepared as in Example 3, as a solid, m.p. 65–83° C. in 49% yield.

$^{13}$C-NMR (δ, CDCl3): 32.92, 41.64, 54.46, 56.44, 77.50, 115.99, 122.48, 125.19, 125.44, 125.47, 126.03, 127.91, 128.68, 128.99, 129.29, 130.00, 131.11, 132.56, 133.06, 133.38, 133.71, 134.03, 139.42, 141.18, 161.51, 166.86, 194.39.

MS (%): 472 (parent+1) and 470 (parent−1) at APCl negative.

Anal. Calc'd for $C_{26}H_{24}NO_4F_3 \cdot HCl \cdot \frac{3}{2}H_2O$: C 58.38, H 5.28, N 2.62. Found: C 58.07, H 5.25, N 2.38.

EXAMPLE 26

({3-[4-(2,4-Difluoro-benzoyl)-phenoxy]-3-phenyl-propyl}-methyl-amino)-acetic Acid Prepared as in Example 3, as an amorphous solid in 28% yield.

$^{13}$C-NMR (δ, CDCl3): 33.23, 41.67, 54.25, 56.42, 104.73 (t, $J_{CF}$=25), 111.99 (d, $J_{CF}$=21), 115.96, 123.54, 123.57, 123.69, 123.73, 125.99, 128.62, 128.99, 129.25, 130.61, 132.20, 132.26, 132.37, 132.41, 139.46, 160.69 (d, $J_{CF}$=247), 161.95, 164.72 (d, $J_{CF}$=247), 167.48, 190.87.

MS (%): 440 (parent+1) at APCl positive

Anal. Calc'd for $C_{25}H_{23}NO_4F_2 \cdot HCl \cdot H_2O \cdot \frac{1}{2}(CH_2Cl_2)$: C 57.10, H 5.07, N 2.61. Found: C 57.32, H 4.93, N 2.76.

EXAMPLE 27

(Methyl-{3-[4-(naphthalene-1-carbonyl)-phenoxy]-3-phenyl-propyl}-amino)-acetic Acid Prepared as in Example 3, as an amorphous solid in 37% yield.

$^{13}$C-NMR (δ, CDCl3): 33.22, 41.59, 54.32, 56.46, 77.48, 115.84, 124.61, 125.72, 126.00, 126.64, 127.20, 127.35, 128.61, 129.22, 130.93, 131.02, 131.55, 132.76, 133.81, 136.74, 139.48, 161.68, 167.11, 196.83.

MS (%): 454 (parent+1) at APCl positive Anal. Calc'd for $C_{29}H_{27}NO_4 \cdot HCl \cdot \frac{3}{2}H_2O$: C 67.37, H 6.04, N 2.71. Found: C 67.58, H 5.85, N 2.67.

EXAMPLE 28

({3-[4-(Benzo[b]thiophene-2-carbonyl)-phenoxy]-3-phenyl-propyl}-methyl-amino)-acetic Acid Prepared as in Example 3, as an amorphous solid in 25% yield.

$^{13}$C-NMR (δ, CDCl3): 33.32, 41.77, 54.30, 56.58, 73.41, 116.07, 122.96, 125.24, 126.10, 126.23, 127.54, 128.60, 129.26, 130.86, 131.13, 131.66, 131.86, 139.22, 139.67, 142.47, 143.12, 161.24, 167.62, 188.33.

MS (%): 460 (parent+1) at APCl positive

Anal. Calc'd for $C_{27}H_{25}NO_4S \cdot HCl \cdot H_2O$: C 63.09, H 5.49, N 2.72. Found: C 63.48, H 5.23, N 2.48.

EXAMPLE 29

({3-[4-(Benzofuran-2-carbonyl)-phenoxy]-3-phenyl-propyl}-methyl-amino)-acetic Acid Prepared as in Example 3, as an amorphous solid in 32% yield.

$^{13}$C-NMR (δ, CDCl3): 33.26, 41.97, 54.43, 56.65, 112.60, 115.83, 116.10, 116.22, 123.19, 123.46, 124.14, 126.07, 127.14, 128.41, 128.61, 128.99, 129.26, 130.36, 131.11, 131.61, 131.86, 139.56, 152.40, 155.95, 161.15, 161.48, 166.79, 167.17, 183.01.

MS (%): 444 (parent+1) at APCl positive

Anal. Calc'd for $C_{27}H_{25}NO_5 \cdot HCl \cdot 3H_2O$: C 60.73, H 6.04, N 2.62. Found: C 60.52, H 5.71, N 2.44.

EXAMPLE 30

({3-[4-(4-Fluoro-benzoyl)-phenoxy]-3-phenyl-propyl}-methyl-amino)-acetic Acid

Prepared as in Example 3, as a solid, m.p. 65–83° C., in 46% yield.

$^{13}$C-NMR (δ, CDCl3): 33.26, 41.69, 54.26, 56.50, 77.58, 115.56 (d, JcF =21), 115.82, 125.76, 125.97, 126.04, 126.21, 128.04, 128.48, 128.60, 129.09, 129.25, 129.75, 130.09, 130.63, 132.32, 132.47, 132.56, 134.18, 139.61, 161.11, 165.28 (d, $J_{CF}$=247), 167.56, 194.17.

MS (%): 422 (parent+1) at APCl positive

Anal. Calc'd for $C_{25}H_{24}NO_4F \cdot HCl \cdot \frac{3}{2}H_2O$: C 61.92, H 5.82, N 2.89. Found: C 61.81, H 5.48, N 2.71.

EXAMPLE 31

({3-[4-(2-Fluoro-benzoyl)-phenoxy]-3-phenyl-propyl}-methyl-amino)-acetic Acid

Prepared as in Example 3, as an amorphous solid in 36.5% yield.

$^{13}$C-NMR (δ, CDCl3): 33.36, 41.70, 54.36, 56.35, 115.96, 116.32 (d, $J_{CF}$=21), 124.49, 125.99, 127.24, 127.39, 128.58, 129.24, 130.60, 132.24, 132.35, 132.89, 139.49, 160.22 (d, $J_{CF}$=247), 161.08, 167.07, 192.09.

MS (%): 422 (parent+1) and 420 (parent-1) at APCl negative.

Anal. Calc'd for $C_{25}H_{24}NO_4F \cdot HCl \cdot 2H_2O$: C 60.79, H 5.92, N 2.84. Found: C 60.80, H 5.49, N 2.99.

EXAMPLE 32

({3-(4-Fluoro-phenyl)-3-[4-(4-methyl-benzoyl)-phenoxy]-propyl}-methyl-amino)-acetic Acid Prepared as in Example 3, as a solid, m.p.60–70° C., in 94% yield.

$^{13}$C-NMR (δ, CDCl3): 21.80, 33.31, 41.69, 54.17, 56.70, 76.82, 115.70, 116.18 (d, $J_{CF}$=21), 127.88, 127.96, 129.14, 130.20, 131.26, 132.33, 135.15, 135.46, 143.20, 160.68, 162.60 (d, $J_{CF}$=247), 167.71, 195.46.

MS (%): 436 (parent+1) at APCl positive

Anal. Calc'd for $C_{26}H_{26}NO_4F_3 \cdot HCl \cdot \frac{3}{2}H_2O$: C 62.58, H 6.06, N 2.81. Found: C 62.20, H 5.85, N 3.03.

EXAMPLE 33

([3-[4-(4-Chloro-benzoyl)-phenoxy]-3-(4-fluoro-phenyl)-propyl]-methyl-amino}-acetic Acid Prepared as in Example 3, as a solid, m.p. 71–85° C., in 100% yield.

$^{13}$C-NMR (δ, CDCl3): 33.25, 41.77, 54.32, 56.62, 115.88, 116.23 (d, $J_{CF}$=21), 127.90, 127.98, 128.79, 130.61, 131.37, 132.38, 135.31, 136.12, 138.84, 160.97, 162.61 (d, $J_{CF}$=247), 167.40, 194.42.

MS (%): 456 (parent+1) at APCl positive.

Anal. Calc'd for $C_{25}H_{23}NO_4FCl \cdot HCl \cdot \frac{1}{2}H_2O$: C 59.89, H 5.03, N 2.79. Found: C 59.89, H 4.90, N 2.69.

EXAMPLE 34

({3-(4-Fluoro-phenyl)-3-[4-(4-trifluoromethyl-benzoyl)-phenoxy]-propyl}-methyl-amino)-acetic Acid Prepared as in Example 3, as a solid, m.p. 58–72° C., in 90% yield.

$^{13}$C-NMR (δ, CDCl3): 33.31, 41.81, 54.24, 57.03, 115.93, 116.27 (d, $J_{CF}$=21), 122.45, 125.17, 125.47, 125.50, 127.84, 127.92, 129.99, 130.17, 132.58, 133.07, 133.47, 133.80, 135.19, 141.10, 143.47, 143.71, 161.42, 162.60 (d, $J_{CF}$=247), 167.90, 194.39.

MS (%): 490 (parent+1) at APCl positive.

Anal. Calc'd for $C_{26}H_{24}NO_4F_3 \cdot HCl$: C 59.30, H 4.85, N 2.32. Found: C 59.38, H 4.60, N 2.66.

EXAMPLE 35

({3-(4-Fluoro-phenyl)-3-[4-(4-methoxy-benzoyl)-phenoxy]-propyl}-methyl-amino)-acetic Acid Prepared as in Example 3, as a solid, m.p. 75–85° C., in 90% yield.

$^{13}$C-NMR (δ, CDCl3): 33.31, 41.75, 54.35, 55.68, 56.56, 113.74, 115.75, 116.16 (d, $J_{CF}$=21), 127.93, 128.02, 130.28, 131.51, 132.10, 132.50, 135.53, 160.50, 163.27, 162.60 (d, $J_{CF}$=247), 167.42, 194.65.

MS (%): 452 (parent+1) at APCl positive.

Anal. Calc'd for $C_{26}H_{26}NO_5F \cdot HCl \cdot \frac{2}{3}H_2O$: C 62.46, H 5.71, N 2.80. Found: C 62.66, H 5.71, N 2.80.

EXAMPLE 36

({3-(4-Fluoro-phenyl)-3-[4-(naphthalene-2-carbonyl)-phenoxy]-propyl}-methyl-amino)-acetic Acid Prepared as in Example 3, a solid, m.p. 87–97° C., in 89% yield.

$^{13}$C-NMR (δ, CDCl3): 33.29, 41.92, 54.46, 56.64, 115.89, 116.21 (d, $J_{CF}$=21), 125.83, 127.03, 127.97, 128.46, 129.50, 131.14, 131.53, 132.35, 132.52, 135.05, 135.25, 135.45, 160.89, 162.60 (d, $J_{CF}$=247), 167.48, 195.74.

MS (%): 472 (parent+1) at APCl positive.

Anal. Calc'd for $C_{29}H_{26}NO_4F \cdot HCl \cdot \frac{5}{4}H_2O$: C 65.66, H 5.61, N 2.64. Found: C 65.67, H 5.61, N 2.62.

EXAMPLE 37

({3-(4-Fluoro-phenyl)-3-[4-(naphthalene-1-carbonyl)-phenoxy]-propyl}-methyl-amino)-acetic Acid Prepared as in Example 3, as a solid, m.p. 91–100° C., in 94% yield.

$^{13}$C-NMR (δ, CDCl3): 33.25, 41.81, 54.30, 56.57, 76.82, 112.50, 115.86, 116.16 (d, $J_{CF}$=21), 124.58, 125.66, 126.66, 127.28, 127.37, 127.86, 127.94, 128.63, 130.92, 131.12, 131.71, 132.76, 133.82, 135.25, 136.60, 161.43, 162.60(d, $J_{CF}$=247), 167.25, 196.84.

MS (%): 472 (parent+1) at APCl positive.

Anal. Calc'd for $C_{29}H_{26}NO_4F \cdot HCl \cdot \frac{5}{4}H_2O$: C 65.66, H 5.61, N 2.64. Found: C 65.75, H 5.71, N 2.71.

EXAMPLE 38

{[3-[4-(2,3-Dimethyl-benzoyl)-phenoxy]-3-(4-fluoro-phenyl)-propyl]-methyl-amino}-acetic Acid Prepared as in Example 3, a solid, m.p. 83–93° C., in 90% yield.

$^{13}$C-NMR (δ, CDCl3): 16.84, 20.31, 33.26, 41.78, 54.29, 56.55, 76.86, 115.82, 116.21 (d, $J_{CF}$=21), 125.26, 125.43, 127.85, 127.93, 131.36, 131.46, 132.55, 134.30, 135.31, 138.00, 139.62, 162.60 (d, $J_{CF}$=247), 167.46, 198.19.

MS (%): 450 (parent+1) at APCl positive.

Anal. Calc'd for $C_{27}H_{28}NO_4F.HCl.\frac{2}{3}H_2O$: C 65.12, H 6.14, N 2.81. Found: C 65.06, H 6.19, N 2.81.

EXAMPLE 39

{[3-[4-(2-Fluoro-benzoyl)-phenoxy]-3-(4-fluoro-phenyl)-propyl]-methyl-amino}-acetic Acid Prepared as in Example 3, a solid, m.p. 65–75° C., in 97% yield.

$^{13}$C-NMR (δ, CDCl3): 33.27, 41.63, 54.14, 56.65, 76.92, 115.95, 116.07, 116.21, 116.28, 116.43, 124.55, 127.16, 127.30, 127.85, 127.93, 130.57, 130.74, 132.29, 132.94, 133.02, 135.35, 158.57, 161.07, 161.34, 161.66, 163.80, 167.62, 192.05.

MS (%): 440 (parent+1) at APCl positive.

Anal. Calc'd for $C_{25}H_{23}NO_4F_2.HCl.\frac{5}{4}H_2O$: C 60.24, H 5.36, N 2.81. Found: C 60.17, H 5.25, N 2.95.

EXAMPLE 40

{[3-[4-(2,4-Difluoro-benzoyl)-phenoxy]-3-(4-fluoro-phenyl)-propyl]-methyl-amino}-acetic Acid Prepared as in Example 3, a solid, m.p. 65–75° C., in 92.5% yield.

$^{13}$C-NMR (δ, CDCl3): 33.28, 41.63, 54.06, 56.90, 104.49, 104.74, 105.00, 111.92, 112.13, 115.96, 116.06, 116.28, 123.42, 123.57, 123.61, 127.87, 127.94, 130.71, 132.20, 132.38, 135.30, 159.31, 159.43, 161.33, 161.67, 161.84, 161.96, 163.43, 163.55, 163.79, 165.97, 166.08, 167.92, 190.88.

MS (%): 458 (parent+1) at APCl positive.

Anal. Calc'd for $C_{25}H_{22}NO_4F_3.HCl.\frac{3}{4}H_2O$: C 59.18, H 4.87, N 2.76. Found: C 59.07, H 4.85, N 2.81.

EXAMPLE 41

({3-(4-Fluoro-phenyl)-3-[4-(3-methyl-benzoyl)-phenoxy]-propyl}-methyl-amino)-acetic Acid Prepared as in Example 3, as a solid, m.p. 75–85, in 94% yield.

$^{13}$C-NMR (δ, CDCl3): 21.51, 33.24, 41.70, 54.25, 56.82, 76.85, 115.75, 116.16 (d, $J_{CF}$=21), 127.20, 127.92, 128.00, 128.26, 130.30, 131.04, 132.45, 133.18, 135.49, 137.92, 138.34, 160.84, 162.60 (d, $J_{CF}$=247), 168.12, 195.88.

MS (%): 436 (parent+1) and x (parent−1) at APCl negative.

Anal. Calc'd for $C_{26}H_{26}NO_4F.HCl.\frac{3}{2}H_2O$: C 62.58, H 6.06, N 2.81. Found: C 62.56, H 5.93, N 2.89.

EXAMPLE 42

({3-(4-Fluoro-phenyl)-3-[4-(thiophene-3-carbonyl)-phenoxy]-propyl}-methyl-amino)-acetic Acid Prepared as in Example 3, as a solid, m.p. 65–75° C., in 92% yield.

$^{13}$C-NMR (δ, CDCl3): 33.25, 41.68, 54.18, 56.56, 76.84, 115.90, 116.16 (d, $J_{CF}$=21), 126.50, 127.93, 128.00, 128.65, 131.75, 131.83, 133.57, 135.49, 141.22, 160.78, 162.60 (d, $J_{CF}$=247), 167.58, 188.91.

MS (%): 428 (parent+1) at APCl positive.

Anal. Calc'd for $C_{23}H_{22}NO_4FS.HCl.\frac{3}{2}H_2O$: C 56.27, H 5.34, N 2.85. Found: C 56.04, H 4.98, N 2.88.

EXAMPLE 43

{[3-[4-(Benzo[b]thiophene-2-carbonyl)-phenoxy]-3-(4-fluoro-phenyl)-propyl]-methyl-amino}-acetic Acid Prepared as in Example 3, as a solid, m.p. 90–100° C., in 89% yield.

$^{13}$C-NMR (δ, CDCl3): 33.43, 41.80, 54.35, 56.51, 116.21 (d, $J_{CF}$=21), 122.96, 125.30, 126.26, 127.63, 128.00, 130.97, 131.65, 131.99, 135.49, 139.19, 142.45, 142.97, 161.04, 162.60 (d, $J_{CF}$=247), 167.34, 188.38.

MS (%): 478 (parent+1) at APCl positive.

Anal. Calc'd for $C_{27}H_{24}NO_4FS.HCl.2H_2O$: C 58.96, H 5.31, N 2.55. Found: C 58.93, H 4.99, N 2.71.

EXAMPLE 44

({3-(4-Fluoro-phenyl)-3-[4-(pyridine-2-carbonyl)-phenoxy]-propyl}methyl-amino)-acetic Acid Prepared as in Example 3, as a solid, m.p. 68–80° C., in 90% yield.

$^{13}$C-NMR (δ, CDCl3): 33.53, 41.74, 53.92, 59.21, 115.54, 116.09 (d, $J_{CF}$=21), 124.71, 126.28, 127.71, 127.79, 129.47, 133.47, 135.53, 135.56, 137.42, 148.47, 155.40, 161.34, 162.56 (d, $J_{CF}$=245), 169.28, 192.57.

MS (%): 423 (parent+1) at APCl positive.

Anal. Calc'd for $C_{24}H_{23}N_2O_4F.HCl.\frac{5}{4}H_2O$: C 59.88, H 5.55, N 5.82. Found: C 59.58, H 5.46, N 5.84.

EXAMPLE 45

({3-(4-Fluoro-phenyl)-3-[4-(thiazole-2-carbonyl)-phenoxy]-propyl}methyl-amino)-acetic Acid Prepared as in Example 3, as a solid, m.p. 98–108° C., in 93% yield.

$^{13}$C-NMR (δ, CDCl3): 33.19, 41.68, 54.25, 56.35, 76.82, 115.96, 116.19 (d, $J_{CF}$=21), 126.29, 127.88, 127.96, 128.57, 133.59, 135.33, 144.83, 161.80, 162.58 (d, $J_{CF}$=248), 167.30, 168.30, 182.49.

MS (%): 429 (parent+1) at APCl positive.

Anal. Calc'd for $C_{22}H_{21}N_2O_4FS.HCl.H_2O$: C 54.71, H 5.01, N 5.80. Found: C 54.71, H 4.99, N 5.69.

EXAMPLE 46

({3-(4-Fluoro-phenyl)-3-[4-(5-methyl-thiazole-2-carbonyl)phenoxy]-propyl}-methyl-amino)-acetic Acid Prepared as in Example 3, as a solid, m.p. 95–110° C., in 81% yield.

$^{13}$C-NMR (δ, CDCl3): 12.63, 33.25, 41.64, 54.09, 56.79, 76.84, 115.88, 116.16 (d, $J_{CF}$=21), 127.87, 127.94, 128.72, 133.42, 135.41, 142.33, 143.20, 161.61, 162.57 (d, $J_{CF}$=247), 166.49, 167.81, 182.55.

MS (%): 443 (parent+1) at APCl positive.

Anal. Calc'd for $C_{23}H_{23}N_2O_4FS.HCl.\frac{1}{2}H_2O$: C 56.61, H 5.16, N 5.74. Found: C 56.67, H 5.22, N 5.50.

EXAMPLE 47

{[3-[4-(Benzothiazole-2-carbonyl)-phenoxy]-3-(4-fluoro-phenyl)propyl]-methyl-amino}-acetic Acid Prepared as in Example 3, as a solid, m.p. 105–11 5° C., in 84% yield.

$^{13}$C-NMR (δ, CDCl3): 33.37, 41.68, 54.02, 57.24, 77.0, 116.00, 116.23 (d, $J_{CF}$=21), 122.32, 125.67, 127.12, 127.73, 127.84, 127.91, 128.37, 133.83, 135.33, 136.98, 153.92, 162.07, 162.60 (d, JCF=248), 167.64, 168.18, 183.51.

MS (%): 479 (parent+1) at APCl positive.

Anal. Calc'd for $C_{26}H_{23}N_2O_4FS.HCl$: C 60.64, H 4.70, N 5.44. Found: C 60.67, H 4.98, N 5.29.

EXAMPLE 48

({3-(4-Fluoro-phenyl)-3-[4-(5-methyl-pyridine-2-carbonyl)phenoxy]-propyl}-methyl-amino)-acetic Acid Prepared as in Example 3, as a solid, m.p. 55–65° C., in 77% yield.

$^{13}$C-NMR (δ, CDCl3): 18.83, 33.55, 41.54, 53.66, 58.49, 76.85, 115.50, 116.10 (d, $J_{CF}$=21), 124.49, 127.78, 127.87, 129.88, 133.45, 135.67, 135.70, 136.62, 137.64, 148.95, 152.96, 161.15, 162.53 (d, $J_{CF}$=247), 168.71, 192.26.

MS (%): 437 (parent+1) at APCl positive.

Anal. Calc'd for $C_{25}H_{25}N_2O_4F$ ¾.HCl.¼H$_2$O: C 64.12, H 5.65, N 5.98. Found: C 64.18, H 5.84, N 5.78.

EXAMPLE 49

({3-(4-Chloro-phenyl)-3-[4-(4-methyl-benzoyl)-phenoxy]-propyl}methyl-amino)-acetic Acid Prepared as in Example 3, as a solid, m.p. 65–71° C., in 50% yield.

$^{13}$C-NMR (δ, CDCl3): 21.85, 33.19, 41.78, 54.25, 56.75, 76.82, 115.73, 127.63, 129.19, 129.43, 130.25, 131.33, 132.38, 134.26, 135.12, 138.31, 143.27, 160.63, 167.73, 195.51.

MS (%): 452/454 (parent+1) at APCl positive.

Anal. Calc'd for $C_{26}H_{26}NO_4Cl.HCl.2H_2O$: C 59.55, H 5.96, N 2.67. Found: C 59.35, H 5.78, N 2.57.

EXAMPLE 50

({3-(4-Chloro-phenyl)-3-[4-(4-methoxy-benzoyl)-phenoxy]-propyl}methyl-amino)-acetic Acid Prepared as in Example 3, as a solid, m.p. 60–70° C., in 61% yield.

$^{13}$C-NMR (δ, CDCl3): 33.20, 41.76, 54.27, 55.69, 56.78, 76.81, 113.77, 115.52, 115.72, 127.52, 127.65, 129.42, 130.31, 131.62, 132.15, 132.52, 134.22, 138.36, 160.43, 163.29, 167.66, 194.59.

MS (%): 468/470 (parent+1) at APCl positive.

Anal. Calc'd for $C_{26}H_{26}NO_5Cl.HCl.¾H_2O$: C 60.30, H 5.55, N 2.70. Found: C 60.15, H 5.66, N 2.56.

EXAMPLE 51

{[3-[4-(4-Chloro-benzoyl)-phenoxy]-3-(4-chloro-phenyl)-propyl]methyl-amino}-acetic Acid Prepared as in Example 3, as a solid, m.p. 63–68° C., in 93% yield.

$^{13}$C-NMR (δ, CDCl3): 33.19, 41.79, 54.31, 56.73, 76.83, 115.88, 127.61, 128.83, 129.48, 130.70, 131.40, 132.41, 134.37, 136.12, 138.12, 138.87, 160.91, 167.40, 189.90, 194.40.

MS (%): 473/475 (parent+1) at APCl positive.

Anal. Calc'd for $C_{25}H_{23}NO_4Cl_2.HCl.¼H_2O$: C 58.49, H 4.81, N 2.73. Found: C 58.25, H 4.97, N 2.59.

EXAMPLE 52

({3-(4-Chloro-phenyl)-3-[4-(4-trifluoromethyl-benzoyl)-phenoxy]propyl}-methyl-amino)-acetic Acid Prepared as in Example 3, as a solid, m.p. 63–70° C., in 87% yield.

$^{13}$C-NMR (δ, CDCl3): 33.12, 41.84, 54.34, 56.51, 76.84, 115.96, 123.82 (q, $J_{CF}$=273), 125.50, 127.59, 129.51, 130.03, 130.27, 132.60, 133.69 (q, $J_{CF}$=33), 134.44, 137.98, 141.05, 161.18, 167.23, 194.40.

MS (%): 506/508 (parent+1) at APCl positive.

Anal. Calc'd for $C_{26}H_{23}NO_4F_3Cl.HCl$: C 57.58, H 4.46, N 2.58. Found: C 57.21, H 4.71, N 2.47.

EXAMPLE 53

({3-(4-Fluoro-phenyl)-3-[4-(3-methyl-pyridine-2-carbonyl)phenoxy]-propyl}-methyl-amino)-acetic Acid Prepared as in Example 3, as a solid, m.p. 65–73° C., in 82% yield.

$^{13}$C-NMR (δ, CDCl3): 18.36, 33.82, 41.70, 53.91, 59.68, 77.27, 115.83, 116.05 (d, $J_{CF}$=22), 124.78, 127.79, 127.87, 129.65, 132.67, 132.92, 135.79, 139.35, 145.92, 155.37, 161.89, 162.50 (d, $J_{CF}$=247), 171.00, 194.13.

MS (%): 437 (parent+1) at APCl positive

Anal. Calc'd for $C_{25}H_{25}N_2O_4F.HCl$: C 63.49, H 5.54, N 5.92. Found: C 63.55, H 5.79, N5.86.

EXAMPLE 54

({3-(4-Chloro-phenyl)-3-[4-(2-fluoro-benzoyl)-phenoxy]-propyl}methyl-amino)-acetic Acid Prepared as in Example 3, as a solid, m.p. 75–85° C., in 91% yield.

$^{13}$C-NMR (δ, CDCl3): 33.26, 41.56, 53.84, 57.35, 77.0, 115.88, 116.33 (d, $J_{CF}$=22), 124.52, 127.19, 127.34, 127.52, 129.42, 130.61, 130.85, 132.34, 132.94, 133.01, 134.28, 138.18, 159.85 (d, $J_{CF}$=251), 161.59, 168.20, 192.04.

MS (%): 456/458 (parent+1) at APCl positive.

Anal. Calc'd for $C_{25}H_{23}NO_4FCl.HCl.⅓H_2O$: C 60.25, H 4.99, N 2.81. Found: C 60.50, H 5.35, N 2.72.

EXAMPLE 55

({3-(4-Chloro-phenyl)-3-[4-(2,4-difluoro-benzoyl)-phenoxy]propyl}-methyl-amino)-acetic Acid Prepared as in Example 3, as a solid, m.p. 75–85° C., in 100% yield.

$^{13}$C-NMR (δ, CDCl3): 33.16, 41.68, 54.13, 56.81, 77.0, 104.77 (t, $J_{CF}$=25), 112.04 (d, $J_{CF}$=21), 115.76, 115.92, 123.55 (dd, $J_{CF}$=3, 15), 127.53, 129.43, 130.85, 132.09, 132.23, 134.27, 134.33, 138.05, 138.19, 160.67 (dd, JCF=12, 255), 161.14, 161.56, 164.80 (dd, $J_{CF}$=12, 255), 167.71, 190.86.

MS (%): 474/476 (parent+1) at APCl positive.

Anal. Calc'd for C25H22NO4F2Cl.HCl.⅔H$_2$O: C 57.48, H 4.70, N 2.68. Found: C 57.84, H 5.00, N 2.57.

EXAMPLE 56

({3-(4-Chloro-phenyl)-3-[4-(2,3-dimethyl-benzoyl)-phenoxy]propyl}-methyl-amino)-acetic Acid Prepared as in Example 3, as a solid, m.p. 85–93° C., in 91% yield.

$^{13}$C-NMR (δ, CDCl3): 16.86, 20.33, 25.80, 33.11, 41.83, 54.28, 56.50, 76.81, 115.81, 125.27, 125.45, 127.56, 129.44, 131.44, 132.58, 134.31, 138.01, 138.08, 139.61, 161.29, 167.28, 198.18.

MS (%): 466/468 (parent+1) at APCl positive.

Anal. Calc'd for $C_{27}H_{28}NO_4Cl.HCl.⅔H_2O$: C 63.04, H 5.94, N 2.72. Found: C 63.28, H 6.33, N 2.50.

EXAMPLE 57

({3-(4-Chloro-phenyl)-3-[4-(thiophene-3-carbonyl)-phenoxy]propyl}-methyl-amino)-acetic Acid Prepared as in Example 3, as a solid, m.p. 91–110° C., in 96% yield.

$^{13}$C-NMR (δ, CDCl3): 33.20, 41.69, 54.10, 56.94, 76.85, 115.85, 126.46, 127.60, 128.69, 129.43, 131.78, 131.98, 133.55, 134.27, 138.27, 141.27, 160.70, 167.89, 188.89.

MS (%): 444/446 (parent+1) at APCl positive.

Anal. Calc'd for $C_{23}H_{22}NO_4ClS·HCl·½H_2O$: C 56.44, H 4.94, N 2.86. Found: C 56.54, H 5.33, N 2.76.

EXAMPLE 58

{[3-[4-(Benzo[b]thiophene-2-carbonyl)-phenoxy]-3-(4-chlorophenyl)-propyl]-methyl-amino}-acetic Acid Prepared as in Example 3, as a solid, m.p. 101–112° C. (from tetrahydrofuran), in 85% yield.

$^{13}$C-NMR (δ, CDCl3): 33.29, 41.64, 53.93, 57.27, 77.0, 116.02, 122.99, 125.27, 126.24, 127.60, 129.44, 131.12, 131.69, 131.91, 134.27, 138.31, 139.21, 142.53, 143.05, 160.95, 168.20, 188.30.

MS (%): 494/496 (parent+1) at APCl positive.

Anal. Calc'd for $C_{27}H_{24}NO_4ClS·HCl·¼H_2O·¼(C_4H_8O)$: C 60.81, H 5.01, N 2.53. Found: C 60.62, H 5.32, N 2.43.

EXAMPLE 59

({3-(4-Fluoro-phenyl)-3-[4-(pyridine-4-carbonyl)-phenoxy]-propyl}methyl-amino)-acetic Acid Prepared as in Example 3, as a solid, m.p. 52–65° C., in 74% yield.

$^{13}$C-NMR (δ, CDCl3): 33.59, 41.64, 53.71, 57.82, 77.09, 116.01, 116.27 (d, $J_{CF}$=25), 122.93, 127.80, 127.88, 129.30, 132.66, 135.31, 145.14, 150.23, 161.70, 162.63 (d, $J_{CF}$=248), 168.46, 193.70.

MS (%): 423 (parent+1) at APCl positive.

Anal. Calc'd for $C_{24}H_{23}N_2O_4F·HCl·⅔H_2O$: C 61.21, H 5.42, N 5.95. Found: C 61.27, H 5.66, N 5.76.

EXAMPLE 60

{[3-[4-(3,5-Bis-trifluoromethyl-benzoyl)-phenoxy]-3-(4-fluorophenyl)-propyl]-methyl-amino}-acetic Acid Prepared as in Example 3, as a solid, m.p. 60–75° C., in 89% yield.

$^{13}$C-NMR (δ, CDCl3): 33.27, 41.82, 54.31, 56.57, 77.01, 116.23, 116.41, 123.05 (q, $J_{CF}$=273), 125.51, 127.86, 127.94, 129.37, 129.65, 132.09 (q, $J_{CF}$=28), 135.05, 139.86, 161.67, 162.69 (d, $J_{CF}$=248), 167.29, 192.33.

MS (%): 558 (parent+1) at APCl positive.

Anal. Calc'd for $C_{27}H_{22}NO_4F_7·½·HCl·H_2O$: C 54.62, H 4.16, N 2.36. Found: C 54.80, H 4.52, N 2.23.

EXAMPLE 61

({3-(4-Chloro-phenyl)-3-[4-(thiazole-2-carbonyl)-phenoxy]-propyl}methyl-amino)-acetic Acid Prepared as in Example 3, as a solid, m.p. 80–100° C., in 96% yield.

$^{13}$C-NMR (δ, CDCl3): 33.13, 41.67, 54.08, 56.80, 76.82, 115.91, 126.29, 127.55, 128.64, 129.43, 133.63, 134.29, 138.12, 144.85, 161.72, 167.77, 168.31, 182.47.

MS (%): 445/447 (parent+1) at APCl positive.

Anal. Calc'd for $C_{22}H_{21}N_2O_4$ Cl·HCl·⅓H_2O: C 54.21, H 4.69, N 5.75. Found: C 54.00, H 4.79, N 5.61.

EXAMPLE 62

({3-(4-Chloro-phenyl)-3-[4-(5-methyl-thiazole-2-carbonyl)phenoxy]-propyl}-methyl-amino)-acetic Acid Prepared as in Example 3, as a solid, m.p. 182–192° C., in 60% yield.

$^{13}$C-NMR (δ, CDCl3): 12.41, 33.32, 41.73, 53.94, 55.67, 76.75, 115.45, 115.69, 127.48, 128.66, 129.33, 133.39, 134.30, 137.88, 142.44, 143.11, 143.17, 161.49, 166.20, 166.3, 182.81.

MS (%): 459/461 (parent+1) at APCl positive.

Anal. Calc'd for $C_{23}H_{23}N_2O_4ClS·HCl·½H_2O$: C 54.76, H 5.00, N 5.55. Found: C 55.10, H 4.84, N 5.21.

EXAMPLE 63

({3-(4-Fluoro-phenyl)-3-[4-(4-isopropyl-benzoyl)-phenoxy]-propyl}methyl-amino)-acetic Acid Prepared as in Example 3, as a solid, m.p. 70–80° C., in 90% yield.

$^{13}$C-NMR (δ, CDCl3): 23.92, 33.35, 34.41, 42.04, 54.59, 56.50, 77.0, 115.55, 115.84, 1 16.21 (d, $J_{CF}$=21), 126.59, 128.05, 130.37, 131.23, 132.38, 135.46, 154.00, 160.72, 162.59 (d, $J_{CF}$=245), 167.12, 195.59.

MS (%): 464 (parent+1) at APCl positive.

Anal. Calc'd for $C_{28}H_{30}NO_4F·HCl·3/2H_2O$: C 63.81, H 6.50, N 2.66. Found: C 63.76, H 6.24, N 2.32.

EXAMPLE 64

({3-(4-Chloro-phenyl)-3-[4-(pyridine-4-carbonyl)-phenoxy]-propyl}methyl-amino)-acetic Acid Prepared as in Example 3, as a solid, m.p. 72–82° C., in 69% yield.

$^{13}$C-NMR (δ, CDCl3): 33.87, 42.00, 53.97, 59.78, 77.0, 115.88, 123.03, 127.34, 129.07,129.39, 132.71, 134.29, 138.25,145.43, 149.99, 161.85,170.74, 193.79.

MS (%): 439/441 (parent+1) at APCl positive.

Anal. Calc'd for $C_{24}H_{23}N_2O_4Cl·½HCl·¾H_2O$: C 61.25, H 5.35, N 5.95. Found: C 61.27, H 5.36, N 5.84.

EXAMPLE 65

{[3-[4-(2,6-Difluoro-benzoyl)-phenoxy]-3-(4-fluorophenyl)propyl]-methyl-amino}-acetic Acid Prepared as in Example 3, as a solid, m.p. 77–87° C., in 96% yield.

$^{13}$C-NMR (δ, CDCl3): 33.15, 41.60, 54.21, 56.56, 77.0, 112.02 (d, $J_{CF}$=24), 116.09, 116.27, 117.08 (t, $J_{CF}$=22), 127.93, 130.40, 132.13, 135.22, 159.70 (d, $J_{CF}$=251), 162.32, 162.59 (d, $J_{CF}$=248), 167.42, 187.51.

MS (%): 458 (parent+1) at APCl positive.

Anal. Calc'd for $C_{25}H_{22}NO_4F_3·HCl·¾H_2O$: C 59.18, H 4.87, N 2.76. Found: C 59.11, H 4.73, N 2.61.

EXAMPLE 66

{[3-(4-Benzoyl-phenoxy)-3-(4-fluoro-phenyl)-propyl]-methyl-amino}acetic Acid

Prepared as in Example 3, as a solid, m.p. 80–95° C., in 82% yield.

$^{13}$C-NMR (δ, CDCl3: 33.34, 41.72, 54.18, 56.79, 76.87, 115.62, 115.75, 116.21 (d, $J_{CF}$=22), 127.86, 127.95, 128.45, 129.91, 130.91, 132.40, 132.49, 135.41, 137.91, 160.86, 162.60 (d, $J_{CF}$=247), 167.78, 195.67.

MS (%): 422 (parent+1) at APCl positive.

Anal. Calc'd for $C_{25}H_{24}NO_4F·HCl·½H_2O$: C 64.31, H 5.61, N 3.00. Found: C 64.41, H 5.33, N 2.53.

EXAMPLE 67

({3-(4-Fluoro-phenyl)-3-[3-(pyridine-4-carbonyl)-phenoxy]-propyl}methyl-amino)-acetic Acid Prepared as in Example 3, as a solid, m.p. 60–70° C., in 90% yield.

$^{13}$C-NMR (δ, CDCl3): 33.85, 41.66, 53.64, 58.75, 77.29, 115.92, 116.24 (d, $J_{CF}$=21), 123.56, 127.74, 127.83, 130.05, 132.53, 133.71, 135.48, 137.20, 150.63, 152.64, 161.49, 162.61 (d, $J_{CF}$=247), 168.86, 193.48.

MS (%): 423 (parent+1) at APCl positive.

Anal. Calc'd for $C_{24}H_{23}N_2O_4F\cdot\frac{1}{3}HCl$: C 6.33, H 5.41, N 6.45. Found: C 66.29, H 5.28, N 6.19.

EXAMPLE 68

({3-(4-Chloro-phenyl)-3-[3-(pyridine-4-carbonyl)-phenoxy]-propyl}methyl-amino)-acetic Acid Prepared as in Example 3, as a solid, m.p. 68–78° C., in 85% yield.

$^{13}$C-NMR (δ, CDCl3): 33.77, 41.70, 53.59, 58.91, 77.14, 115.89, 123.56, 127.45, 129.45, 130.10, 132.55, 133.69, 134.31, 137.18, 138.33, 150.64, 152.67, 161.44, 168.99, 193.46.

MS (%): 438/440 (parent+1) at APCl positive.

Anal. Calc'd for $C_{24}H_{23}N_2O_4Cl\cdot\frac{1}{2}HCl$: C 63.06, H 5.18, N 6.13. Found: C 63.12, H 5.10, N 6.10.

What is claimed is:

1. A compound of the formula I

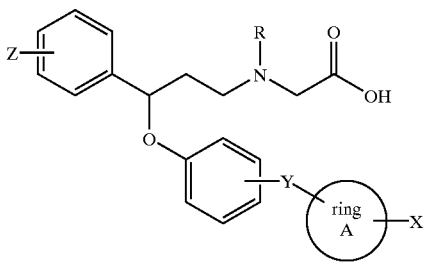

wherein ring A is phenyl, naphthyl, benzothienyl, benzofuranyl, or thienyl; or ring A is a monocyclic aryl or heteroaryl ring containing from zero to four heteroatoms and not containing any adjacent ring oxygen atoms; or ring A is a bicyclic aryl or heteroaryl ring containing from zero to five heteroatoms and not containing any adjacent ring oxygen atoms; and Y is C=O or $SO_2$ and is attached to the phenoxy group depicted in formula I at the meta or para position;

X and Z are independently selected from hydrogen, ($C_1$–$C_6$) alkyl optionally substituted with from one to seven fluorine atoms, and ($C_1$–$C_6$)alkoxy optionally substituted with from one to seven fluorine atoms, wherein the number of fluorine substituents on the foregoing ($C_1$–$C_6$) alkyl and ($C_1$–$C_6$) alkoxy groups can not exceed the number of positions in such groups that are available for substitution;

or X and Z are independently selected from carboxy, carbo-($C_1$–$C_6$)alkoxy, carboxamido, ($C_1$–$C_6$)alkylthio, sulfoxyl, sulfonyl, halo, nitro, cyano, amino, ($C_1$–$C_6$) alkylamino and di[($C_1$–$C_6$) alkyl]amino; and R is hydrogen or ($C_1$ to $C_6$) alkyl, hydrogen or methyl;

or a pharmaceutically acceptable salt thereof.

2. A compound according to claim 1, wherein ring A is selected from phenyl, naphthyl and benzothienyl.

3. A compound according to claim 1, wherein X is para-trifluoromethyl, para-methyl or para-chloro.

4. A compound according to claim 1, wherein Y is C=O.

5. A compound according to claim 1, wherein Y is $SO_2$.

6. A method of treating a disorder or condition selected from mood disorders, single episodic or recurrent major depressive disorder, dysthymic disorder, depressive neurosis and neurotic depression, melancholic depression, atypical depression, seasonal affective disorder, pediatric depression, bipolar disorders, bipolar I disorder, bipolar II disorder, cyclothymic disorder, conduct disorder, disruptive behavior disorder, anxiety disorders, panic disorder with or without agoraphobia, agoraphobia without history of panic disorder, specific phobias, social anxiety, social phobia, obsessive-compulsive disorder, stress disorders, post-traumatic stress disorder, acute stress disorder, generalized anxisty disorder, borderline personality disorder, psychosis, schizophrenia, conduct disorder, disruptive behavior disorder, psychotic episodes of anxiety, anxiety associated with psychosis, psychotic mood disorders; mood disorders associated with psychotic disorders, behavioral manifestations of mental retardation, conduct disorder and autistic disorder; movement disorders; attention deficit hyperactivity disorder; and cognitive disorders in a mammal in need of such treatment, comprising administering to the mammal an amount of the compound of formula I that is effective in treating such condition or disorder.

7. A pharmaceutical composition for treating a disorder or condition selected from mood disorders, single episodic or recurrent major depressive disorder, dysthmic disorder, depressive neurosis and neurotic depression, melancholic depression, atypical depression, seasonal affective disorder, pediatric depression, bipolar disorders, bipolar I disorder, bipolar II disorder, cyclothymic disorder, conduct disorder, disruptive behavior disorder, anxiety disorders, panic disorders with or without agoraphobia, agoraphobia without history of panic disorder, specific phobias, social anxiety, social phobia, obsessive-compulsive disorder, stress disorders, post-traumatic stress disorder, acute stress disorder, generalized anxiety disorder, borderline personality disorder, psychosis, schizophrenia, conduct disorder, disruptive behavior disorder, psychotic episodes of anxiety, anxiety associated with psychosis, psychotic mood disorders; mood disorders associated with psychotic disorders, behavioral manifestations of mental retardation, conduct disorder and autistic disorder; movement disorders; attention deficit hyperactivity disorder; and cognitive disorders in a mammal in need of such treatment, comprising an amount of the compound of formula I that is effective in treating such disorder or condition.

8. A method of treating a disorder or condition selected from mood disorders, single episodic or recurrent major depressive disorder, dysthymic disorder, depressive neurosis and neurotic depression, melancholic depression, atypical depression, seasonal affective disorder, pediatric depression, bipolar disorders, bipolar I disorder, bipolar II disorder, cyclothymic disorder, conduct disorder, disruptive behavior disorder, anxiety disorders, panic disorder with or without agoraphobia, agoraphobia without history of panic disorder, specific phobias, social anxiety, social phobia, obsessive-compulsive disorder, stress disorders, post-traumatic stress disorder, acute stress disorder, generalized anxiety disorder, borderline personality disorder, psychosis, schizophrenia, conduct disorder, disruptive behavior disorder, psychotic episodes of anxiety, anxiety associated with psychosis, psychotic mood disorders; mood disorders associated with psychotic disorders, behavioral manifestations of mental retardation, conduct disorder and autistic disorder; movement disorders; attention deficit hyperactivity disorder; and cognitive disorders in a mammal, including a human in need of such treatment, comprising administering to a mammal a glycine transport inhibiting amount of the compound of formula I.

9. A pharmaceutical composition for treating a disorder or condition selected from mood disorders, single episodic or recurrent major depressive disorder, dysthymic disorder, depressive neurosis and neurotic depression, melancholic depression, atypical depression, seasonal affective disorder, pediatric depression, bipolar disorders, bipolar I disorder, bipolar II disorder, cyclothymic disorder, conduct disorder, disruptive behavior disorder, anxiety disorders, panic disorder with or without agoraphobia, agoraphobia without history of panic disorder, specific phobias, social anxiety, social phobia, obsessive-compulsive disorder, stress disorders, post-traumatic stress disorder, acute stress disorder, generalized anxiety disorder, borderline personality disorder, psychosis, schizophrenia, conduct disorder, disruptive behavior disorder, psychotic episodes of anxiety, anxiety associated with psychosis, psychotic mood disorders; mood disorders associated with psychotic disorders, behavioral manifestations of mental retardation, conduct disorder and autistic disorder; movement disorders; attention deficit hyperactivity disorder; and cognitive disorders in a mammal, including a human, comprising a glycine transport inhibiting amount of a compound of formula I.

10. The method of claim 6, wherein said psychotic mood disorders are selected from the group consisting of severe major depressive disorder; wherein said mood disorders associated with psychotic disorders are selected from the group consisting of acute mania or depression associated with bipolar disorder and mood disorders associated with schizophrenia; wherein said movement disorders are selected from the group consisting of Tourette's syndrome, akinetic-rigid syndrome, movement disorders associated with Parkinson's disease, drug induced and neurodegeneration based dyskinesias; or, wherein said cognitive disorders are selected from the group consisting of dementias and memory disorders.

11. The method of claim 10, wherein said drug induced and neurodegeneration based dyskinesia is selected from the group consisting of tardive dyskinesia; or wherein said dementia is selected from the group consisting of age related dementia, HIV-1 associated dementia, AIDS dementia complex (ADC), HIV encephalopathy and senile dementia of the Alzheimer's type.

12. The pharmaceutical composition of claim 7, wherein said psychotic mood disorders are selected from the group consisting of severe major depressive disorder; wherein said mood disorders associated with psychotic disorders are selected from the group consisting of acute mania or depression associated with bipolar disorder and mood disorders associated with schizophrenia; wherein said movement disorders are selected from the group consisting of Tourette's syndrome, akinetic-rigid syndrome, movement disorders associated with Parkinson's disease, drug induced and neurodegeneration based dyskinesias; or, wherein said cognitive disorders are selected from the group consisting of dementias and memory disorders.

13. The pharmaceutical composition of claim 12, wherein said drug induced and neurodegeneration based dyskinesia is selected from the group consisting of tardive dyskinesia is selected from the group consisting of tardive dykinesia; or wherein said dementia is selected from the group consisting of age related dementia, HIV-1 associated dementia, AIDS dementia complex (ADC), HIV encephalopathy and senile dementia of the Alzheimer's type.

14. The method of claim 8, wherein said psychotic mood disorders are selected from the group consisting of severe major depressive disorder; wherein said mood disorders associated with psychotic disorders are selected from the group consisting of acute mania or depression associated with bipolar disorder and mood disorders associated with schizophrenia; wherein said movement disorders are selected from the group consisting of Tourette's syndrome, akinetic-rigid syndrome, movement disorders associated with Parkinson's disease, drug induced and neurodegeneration based dyskinesias; or, wherein said cognitive disorders are selected from the group consisting of dementias and memory disorders.

15. The method of claim 14, wherein said drug induced and neurodegeneration based dyskinesia is selected from the group consisting of tardive dyskinesia; or wherein said dementia is selected from the group consisting of age related dementia, HIV-1 associated dementia, AIDS dementia complex (ADC), HIV encephalopathy and senile dementia of the Alzheimer's type.

16. The pharmaceutical composition of claim 9, wherein said psychotic mood disorders are selected from the group consisting of severe major depressive disorder; wherein said mood disorders associated with psychotic disorders are selected from the group consisting of acute mania or depression associated with bipolar disorder and mood disorders associated with schizophrenia; wherein said movement disorders are selected from the group consisting of Tourette's syndrome, akinetic-rigid syndrome, movement disorders associated with Parkinson's disease, drug induced and neurodegeneration based dyskinesias; or, wherein said cognitive disorders are selected from the group consisting of dementias and memory disorders.

17. The pharmaceutical composition of claim 16, wherein said drug induced and neurodegeneration based dyskinesia is selected from the group consisting of tardive dyskinesi; or wherein said dementia is selected from the group consisting of age related dementia, HIV-1 associated dementia, AIDS dementia complex (ADC), HIV encephalopathy and senile dementia of the Alzheimer's type.

* * * * *